(12) United States Patent
Brummerhop et al.

(10) Patent No.: US 7,820,804 B2
(45) Date of Patent: *Oct. 26, 2010

(54) FLUOROGLYCOSIDE DERIVATIVES OF PYRAZOLES, MEDICAMENTS CONTAINING THESE COMPOUNDS, AND THE USE THEREOF

(75) Inventors: Harm Brummerhop, Frankfurt (DE); Wendeline Frick, Hunstetten-Beuerbach (DE); Heiner Glombik, Hofheim (DE); Oliver Plettenburg, Kelkheim (DE); Martin Bickel, Bad Homburg (DE); Hubert Heuer, Schwabenheim (DE); Stefan Theis, Frankfurt (DE)

(73) Assignee: Sanofi-Aventia Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/567,410

(22) Filed: Dec. 6, 2006

(65) Prior Publication Data

US 2007/0197623 A1 Aug. 23, 2007

Related U.S. Application Data

(63) Continuation of application No. PCT/EP2005/005959, filed on Jun. 3, 2005.

(30) Foreign Application Priority Data

Jun. 11, 2004 (DE) ................. 10 2004 028 241

(51) Int. Cl.
*C07H 17/02* (2006.01)
*C07H 17/00* (2006.01)
*A61K 31/7056* (2006.01)

(52) U.S. Cl. ............. 536/17.4; 536/17.5; 536/29.11; 514/27; 514/24; 514/42

(58) Field of Classification Search .......... 536/17.4, 536/17.5, 29.11; 514/24, 27, 42
See application file for complete search history.

(56) References Cited

U.S. PATENT DOCUMENTS

2004/0006025 A1 * 1/2004 Ohsumi et al. ............. 514/23
2004/0259819 A1 * 12/2004 Frick et al. ................ 514/43

FOREIGN PATENT DOCUMENTS

| EP | 0850948 | 7/1998 |
|---|---|---|
| EP | 1213296 | 6/2002 |
| WO | WO 2004/052903 | 6/2004 |

OTHER PUBLICATIONS

Du et al. Tetrahedron, 1998, 54, p. 9913-9959.*
Diez-Sampedro, A., et. al., Residue 457 Controls Sugar Binding and Transport in the Na+/Glucose Cotransporter, The Journal of Biological Chemistry vol. 276, No. 52, Issue of Dec. 28, pp. 49188-49194, (2001).

* cited by examiner

*Primary Examiner*—Shaojia Anna Jiang
*Assistant Examiner*—Jonathan S Lau
(74) *Attorney, Agent, or Firm*—Barbara E. Kurys

(57) ABSTRACT

The invention relates to substituted fluoroglycoside derivatives of pyrazoles of formula (I) as further defined in the specification, to the physiologically compatible salts thereof, to a method for their production, and to their use as antidiabetics.

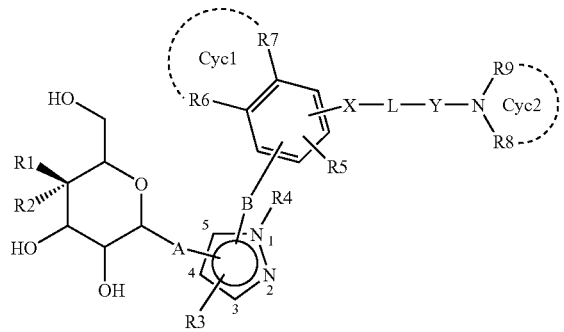

15 Claims, No Drawings

FLUOROGLYCOSIDE DERIVATIVES OF PYRAZOLES, MEDICAMENTS CONTAINING THESE COMPOUNDS, AND THE USE THEREOF

CROSS-REFERENCE TO RELATED APPLICATIONS

This application is a continuation of PCT/EP2005/005959, filed 3 Jun. 2005, which claims priority from German Patent Application No. DE 10 2004 028 241.2, filed 11 Jun. 2004.

SUMMARY OF THE INVENTION

The invention relates to substituted fluoroglycoside derivatives of pyrazoles, their physiologically tolerated salts and physiologically functional derivatives.

BACKGROUND OF THE INVENTION

Several classes of substances having an SGLT effect have been disclosed in the literature. The model for all these structures was the natural product phlorizin. From this were derived the following classes which are described in the property rights below:
- propiophenone glycosides of Tanabe (WO 0280936, WO 0280935, JP 2000080041 and EP 850948)
- 2-(glucopyranosyloxy)benzylbenzenes of Kissei (WO 0244192, WO 0228872, WO 03011880 and WO 0168660)
- glucopyranosyloxypyrazoles of Kissei, Bristol-Myers Squibb and Ajinomoto (WO 02068440, WO 02068439, WO 0236602, WO 01016147, WO 02053573, WO 03020737, WO 03090783, WO 04014932, WO 04019958 and WO 04018491)
- O-glycoside benzamides of Bristol-Meyers Squibb (WO 0174835 and WO 0174834)
- glucopyranosyloxythiophenes of Aventis (WO 04007517) and C-aryl glycosides of Bristol-Meyers Squibb (WO 03099836, WO 0127128 and US 2002137903).

All the known structures contain glucose as a very important structural element.

The invention was based on the object of providing novel compounds with which it is possible to prevent and treat type 1 and type 2 diabetes. We have now surprisingly found that fluoroglycoside derivatives of pyrazoles increase the effect on SGLT. These compounds are therefore particularly suitable for preventing and treating type 1 and type 2 diabetes.

DETAILED DESCRIPTION OF THE INVENTION

The invention therefore relates to compounds of the formula I

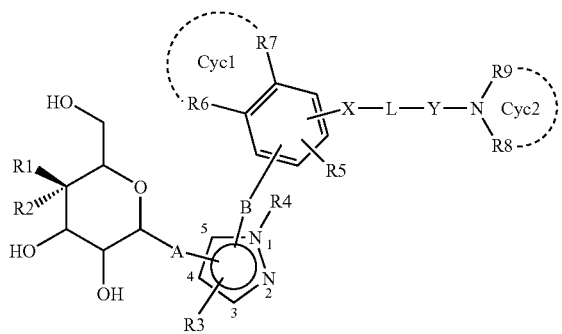

I in which the meanings are

R1 and R2 independently of one another F or H, where one of the radicals R1 or R2 must be F;

A O, NH, $CH_2$, S or a bond;

R3 hydrogen, F, Cl, Br, I, OH, $CF_3$, $NO_2$, CN, COOH, CO—$(C_1$-$C_6)$-alkyl, COO$(C_1$-$C_6)$-alkyl, $CONH_2$, CONH—$(C_1$-$C_6)$-alkyl, CON[$(C_1$-$C_6)$-alkyl]$_2$, $(C_1$-$C_6)$-alkyl, $(C_3$-$C_6)$-cycloalkyl, $(C_2$-$C_6)$-alkenyl, $(C_2$-$C_6)$-alkynyl, O—$(C_1$-$C_6)$-alkyl, HO—$(C_1$-$C_6)$-alkylene, $(C_1$-$C_6)$-alkylene-O—$(C_1$-$C_6)$-alkyl, phenyl, benzyl, $(C_1$-$C_6)$-alkoxycarbonyl, where one, more than one or all hydrogen(s) in the alkyl, alkenyl, alkynyl and O-alkyl radicals may be replaced by fluorine;

$SO_2$—$NH_2$, $SO_2$—NH$(C_1$-$C_6)$-alkyl, $SO_2$N[$(C_1$-$C_6)$-alkyl]$_2$, S—$(C_1$-$C_6)$-alkyl, S—$(CH_2)_o$-phenyl, SO—$(C_1$-$C_6)$-alkyl, SO—$(CH_2)_o$-phenyl, $SO_2$—$(C_1$-$C_6)$-alkyl, $SO_2$—$(CH_2)_o$-phenyl, where o may be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$NH_2$, NH—$(C_1$-$C_6)$-alkyl, N($(C_1$-$C_6)$-alkyl)$_2$, NH—CO—$(C_1$-$C_7)$-alkyl, phenyl, O—$(CH_2)_o$-phenyl, where o may be 0-6, where the phenyl ring may be substituted one to three times by F, Cl, Br, I, OH, $CF_3$, $NO_2$, CN, $OCF_3$, O—$(C_1$-$C_6)$-alkyl, $(C_1$-$C_6)$-alkyl, $NH_2$, NH$(C_1$-$C_6)$-alkyl, N($(C_1$-$C_6)$-alkyl)$_2$, $SO_2$—$CH_3$, COOH, COO—$(C_1$-$C_6)$-alkyl, $CONH_2$;

R4 hydrogen, $(C_1$-$C_6)$-alkyl, $(C_2$-$C_6)$-alkenyl, $(C_3$-$C_6)$-cycloalkyl, or phenyl that may optionally be substituted by halogen or $(C_1$-$C_4)$-alkyl;

B $(C_0$-$C_{15})$-alkylene, where one or more C atoms of the alkylene radical may be replaced independently of one another by —O—, —(C=O)—, —CH=CH—, —C≡C—, —S—, —CH(OH)—, —CHF—, —$CF_2$—, —(S=O)—, —($SO_2$)—, —N(($C_1$-$C_6)$-alkyl)-, —N(($C_1$-$C_6)$-alkylphenyl)- or —NH—;

R5, R6, R7 independently of one another, hydrogen, F, Cl, Br, I, OH, $CF_3$, $NO_2$, CN, COOH, COO$(C_1$-$C_6)$-alkyl, CO$(C_1$-$C_4)$-alkyl, $CONH_2$, CONH$(C_1$-$C_6)$-alkyl, CON[$(C_1$-$C_6)$-alkyl]$_2$, $(C_1$-$C_6)$-alkyl, $(C_2$-$C_6)$-alkenyl, $(C_2$-$C_6)$-alkynyl, O—$(C_1$-$C_8)$-alkyl, HO—$(C_1$-$C_6)$-alkylene, $(C_1$-$C_6)$-alkylene-O—$(C_1$-$C_6)$-alkyl, where one, more than one, or all hydrogen(s) in the alkyl, alkenyl, alkynyl and O-alkyl radicals may be replaced by fluorine;

$SO_2$—$NH_2$, $SO_2$NH$(C_1$-$C_6)$-alkyl, $SO_2$N[$(C_1$-$C_6)$-alkyl]$_2$, S—$(C_1$-$C_6)$-alkyl, S—$(CH_2)_o$-phenyl, $SCF_3$, SO—$(C_1$-$C_6)$-alkyl, SO—$(CH_2)_o$-phenyl, $SO_2(C_1$-$C_6)$-alkyl, $SO_2$-$(CH_2)_o$-phenyl, where o may be 0-6, and the phenyl ring may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$NH_2$, NH—$(C_1$-$C_6)$-alkyl, N($(C_1$-$C_6)$-alkyl)$_2$, NH—CO—$(C_1$-$C_6)$-alkyl, phenyl, O—$(CH_2)_o$-phenyl, where o may be 0-6, where the phenyl ring may be substituted one to three times by F, Cl, Br, I, OH, $CF_3$, $NO_2$, CN, $OCF_3$, O—$(C_1$-$C_8)$-alkyl, $(C_1$-$C_6)$-alkyl, $NH_2$, NH$(C_1$-$C_6)$-alkyl, N($(C_1$-$C_6)$-alkyl)$_2$, $SO_2$—$CH_3$, COOH, COO—$(C_1$-$C_6)$-alkyl, $CONH_2$;

or

R6 and R7 together with the C atoms carrying them a 5 to 7 membered, saturated, partially or completely unsaturated ring Cyc1, where 1 or 2 C atom(s) of the ring may also be replaced by N, O or S, and Cyc1 may optionally be substituted by $(C_1$-$C_6)$-alkyl, $(C_2$-$C_5)$-alkenyl, $(C_2$-$C_5)$-alkynyl, where in each case one $CH_2$ group may be replaced by O, or substituted by H, F, Cl, OH, $CF_3$, $NO_2$, CN, COO$(C_1$-$C_4)$-alkyl, $CONH_2$, CONH$(C_1$-$C_4)$-alkyl, $OCF_3$;

X CO, O, NH, S, SO, $SO_2$ or a bond;
L $(C_1-C_6)$-alkylene, $(C_2-C_5)$-alkenylene, $(C_2-C_5)$-alkynylene, where in each case one or two $CH_2$ group(s) may be replaced by O or NH;
Y CO, NHCO, SO, $SO_2$, or a bond;
R8, R9 independently of one another, hydrogen, $SO_3H$, sugar residue, $(C_1-C_6)$-alkyl, where one or more $CH_2$ groups of the alkyl radical may be substituted independently of one another by $(C_1-C_6)$-alkyl, OH, $(C_1-C_6)$-alkylene-OH, $(C_2-C_6)$-alkenylene-OH, O-sugar residue, $OSO_3H$, $NH_2$, NH—$(C_1-C_6)$-alkyl, $N[(C_1-C_6)$-alkyl$]_2$, NH—CO—$(C_1-C_6)$-alkyl, NH-sugar residue, NH—$SO_3H$, $(C_1-C_6)$-alkylene-$NH_2$, $(C_2-C_6)$-alkenylene-$NH_2$, $(C_0-C_6)$-alkylene-COOH, $(C_0-C_6)$-alkylene-$CONH_2$, $(C_0-C_6)$-alkylene-CONH—$(C_1-C_6)$-alkyl, $(C_0-C_6)$-alkylene-$SONH_2$, $(C_0-C_6)$-alkylene-SONH—$(C_1-C_6)$-alkyl, $(C_0-C_6)$-alkylene-$SO_2NH_2$, $(C_0-C_6)$-alkylene-$SO_2N$ H—$(C_1-C_6)$-alkyl, adamantyl; or
R8 and R9 together with the N atom carrying them form a 5 to 7 membered, saturated ring Cyc2, where one or more $CH_2$ groups of the ring may also be replaced by O, S, NH, $NSO_3H$, N-sugar residue, N—$(C_1-C_6)$-alkyl, where one or more $CH_2$ groups of the alkyl radical may be substituted independently of one another by $(C_1-C_6)$-alkyl, OH, $(C_1-C_6)$-alkylene-OH, $(C_2C_6)$-alkenylene-OH, $NH_2$, NH—$(C_1-C_6)$-alkyl, $N[(C_1-C_6)$-alkyl$]_2$, NH—CO—$(C_1-C_6)$-alkyl, NH-sugar residue, $(C_1-C_6)$-alkylene-$NH_2$, $(C_2-C_6)$-alkenylene-$NH_2$, $(C_0-C_6)$-alkylene-COOH, $(C_0-C_6)$-alkylene-$CONH_2$, $(C_0-C_6)$-alkylene-CONH—$(C_1-C_6)$-alkyl, $(C_0-C_6)$-alkylene-$SONH_2$, $(C_0-C_6)$-alkylene-SONH—$(C_1-C_6)$-alkyl, $(C_0-C_6)$-alkylene-$SO_2NH_2$, $(C_0-C_6)$-alkylene-$SO_2NH$—$(C_1-C_6)$-alkyl;

and the pharmaceutically acceptable salts thereof.

Sugar residues mean compounds derived from aldoses and ketoses having 3 to 7 carbon atoms, which may belong to the D or L series; also included therein are aminosaccharides, sugar alcohols or saccharic acids (Jochen Lehmann, Chemie der Kohlenhydrate, Thieme Verlag 1976). Examples which may be mentioned are glucose, mannose, fructose, galactose, ribose, erythrose, glyceraldehyde, sedoheptulose, glucosamine, galactosamine, glucuronic acid, galacturonic acid, gluconic acid, galactonic acid, mannonic acid, glucamine, 3-amino-1,2-propanediol, glucaric acid and galactaric acid. The compounds may moreover occur in the alpha and beta forms.

The points of linkage of A, B, R3 and R5 to the ring can be chosen without restriction. All resulting compounds of the formula I are included in the present invention.

Preference is given to compounds of the formula I in which the meanings are
A O, NH, a bond;
R3 hydrogen, F, Cl, Br, I, OH, $CF_3$, $NO_2$, CN, COOH, CO—$(C_1-C_6)$-alkyl, COO$(C_1-C_6)$-alkyl, $CONH_2$, CONH—$(C_1-C_6)$-alkyl, CON$[(C_1-C_6)$-alkyl$]_2$, $(C_1-C_6)$-alkyl, $(C_2-C_6)$-alkenyl, $(C_2-C_6)$-alkynyl, O—$(C_1-C_6)$-alkyl, HO—$(C_1-C_6)$-alkylene, $(C_1-C_6)$-alkylene-O—$(C_1-C_6)$-alkyl, phenyl, benzyl, $(C_1-C_4)$-alkylene-COOH, SO—$(C_1-C_6)$-alkyl, where one, more than one or all hydrogen(s) in the alkyl radicals may be replaced by fluorine; or
R4 hydrogen, $(C_1-C_6)$-alkyl, $(C_2-C_6)$-alkenyl, $(C_3-C_6)$-cycloalkyl;
B $(C_0-C_6)$-alkylene, where one or more C atom(s) of the alkylene radical may be replaced independently of one another by —O—, —(C=O)—, —CH=CH—, —C≡C—, —S—, —CH(OH)—, —CHF—, —$CF_2$—, —(S=O)—, —($SO_2$)—, —N(($C_1-C_6$)-alkylene-, —N(($C_1-C_6$)-alkylene-phenylene)- or —NH—.

Further preferred compounds of the formula I are those in which the sugar residues are beta(β)-linked, and the stereochemistry in the 2, 3 and 5 positions of the sugar residue has the D-gluco configuration.

Preference is further given to compounds of the formula I in which
R1 is hydrogen and
R2 is fluorine;
or
R1 is fluorine and
R2 is hydrogen;
A is O, NH;
R3 is hydrogen, F, Cl, Br, I, OH, $CF_3$, $(C_1-C_6)$-alkyl, $(C_3-C_6)$-cycloalkyl, $(C_2-C_6)$-alkenyl, O—$(C_1-C_6)$-alkyl, where one, more than one or all hydrogen(s) in the alkyl radicals may be replaced by fluorine;
R4 is hydrogen, $(C_1-C_6)$-alkyl, $(C_3-C_6)$-cycloalkyl;
B is $(C_0-C_4)$-alkylene, where one or more C atom(s) of the alkylene radical may be replaced independently of one another by —O—, —(C=O)—, —CH=CH—, —CH(OH)—, —CHF—, —$CF_2$— or —NH—;
R5, R6, R7 independently of one another, are hydrogen, F, Cl, Br, I, OH, $CF_3$, $NO_2$, CN, COOH, COO$(C_1-C_6)$-alkyl, CO$(C_1-C_4)$-alkyl, $CONH_2$, CONH$(C_1-C_6)$-alkyl, CON$[(C_1-C_6)$-alkyl$]_2$, $(C_1-C_6)$-alkyl, $(C_2-C_6)$-alkenyl, $(C_2-C_6)$-alkynyl, O—$(C_1-C_8)$-alkyl, HO—$(C_1-C_6)$-alkylene, $(C_1-C_6)$-alkylene-O—$(C_1-C_6)$-alkyl, where one, more than one, or all hydrogen(s) in the alkyl, alkenyl, alkynyl and O-alkyl radicals may be replaced by fluorine; $NH_2$, NH—$(C_1-C_6)$-alkyl, N(($C_1-C_6$)-alkyl$)_2$, NH—CO—$(C_1-C_6)$-alkyl, or
R6 and R7 together with the C atoms carrying them are a 5 to 7 membered, saturated, partially or completely unsaturated ring Cyc1, where 1 or 2 C atom(s) of the ring may also be replaced by N, O or S, and Cyc1 may optionally be substituted by $(C_1-C_6)$-alkyl, $(C_2-C_5)$-alkenyl, $(C_2-C_5)$-alkynyl, where in each case one $CH_2$ group may be replaced by O, or substituted by H, F, Cl, OH, $CF_3$, $NO_2$, CN, COO$(C_1-C_4)$-alkyl, $CONH_2$, CONH$(C_1-C_4)$-alkyl, $OCF_3$;
X is CO, O, NH, a bond;
L is $(C_1-C_6)$-alkylene, $(C_2-C_5)$-alkenylene, where in each case one or two $CH_2$ group(s) may be replaced by O or NH;
Y is CO, NHCO, a bond.

Particular preference is given to compounds of the formula I in which
R1 is hydrogen;
R2 is fluorine;
A is O;
R3 is $CF_3$, methyl, isopropyl;
R4 is hydrogen;
B is $(C_0-C_4)$-alkylene, where one or more C atom(s) of the alkylene radical may be replaced independently of one another by —O—, —(C=O)—, —CHF— or —$CF_2$—;
X is CO, O, a bond;
L is $(C_1-C_4)$-alkylene, $(C_2-C_4)$-alkenylene, where in each case one or two $CH_2$ group(s) may be replaced by O or NH;
Y is CO, NHCO, a bond.

Very particular preference is given to compounds of the formula I in which
R1 is hydrogen;
R2 is fluorine;
A is O;
B is —$CH_2$—;
R5 is hydrogen, Cl, methyl, ethyl, OH, $CF_3$;
R6, R7 are hydrogen;

X is CO, O, a bond;

L is $(C_1-C_3)$-alkylene, $(C_2-C_3)$-alkenylene, where in each case one $CH_2$ group may be replaced by O or NH;

Y is CO, NHCO, a bond.

Particularly preferred compounds of the formula I are those in which the substituents A and B occupy an adjacent position (ortho position) and R3 occupies an adjacent position (ortho position) to B.

Very particular preference is further given to compounds of the formula I in which R8, R9 independently of one another, are hydrogen, $SO_3H$, sugar residue, $(C_1-C_4)$-alkyl, where the alkyl radical may be substituted independently of one another one or more times by $(C_1-C_2)$-alkyl, OH, $(C_1-C_2)$-alkylene-OH, $OSO_3H$, $NH_2$, $CONH_2$, $SO_2NH_2$, NH—$SO_3H$ or adamantyl;

or

R8 and R9 together with the N atom carrying them form a 5 to 7 membered, saturated ring Cyc2, selected from the group of piperazine which may be N-substituted by $(C_1-C_2)$-alkyl, $(C_1-C_2)$-alkylene-OH or $SO_3H$, piperidine, azepane, pyrrolidine or morpholine.

In a particular embodiment of the compounds of the formula I, the substituents B and X are disposed in para position on the phenyl ring.

In a further embodiment of the compounds of formula I, the substituents A are disposed in position 3, B in position 4 and R3 in position 5 on the pyrazole ring.

In a further embodiment of the compounds of formula I, the substituents A are disposed in position 5, B in position 4 and R3 in position 3 on the pyrazole ring.

The alkyl radicals in the substituents R3, R4, R5, R6, R7, R8 and R9 may be either straight-chain or branched. Halogen means F, Cl, Br, I, preferably F and Cl.

The invention relates to compounds of the formula I in the form of their tautomers, racemates, racemic mixtures and pure enantiomers, and to their diastereomers and mixtures thereof. The present invention includes all these isomeric and, where appropriate, tautomeric forms of the compounds of the formula I. These isomeric forms can be obtained by known methods even if not (in some cases) expressly described.

Pharmaceutically acceptable salts are, because their solubility in water is greater than that of the starting or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention further relates to the use of compounds of the formula I and their pharmaceutical compositions for inhibiting SGLT 1 (sodium dependent glucose transporter 1). SGLT 1 is involved in the intestinal uptake of carbohydrates, in particular the intestinal uptake of glucose (E. Turk et al., Nature 1991, 350, 354-356). Inhibition of the absorption of glucose inhibits the rise in the blood glucose concentration. Thus, inhibitors of SGLT 1 are suitable for the treatment, control and prophylaxis of metabolic disorders, especially of diabetes mellitus.

The compounds of the formula I are distinguished by beneficial effects on glucose metabolism; in particular, they lower the blood glucose level and are suitable for the treatment of type 1 and type 2 diabetes. The compounds can therefore be employed alone or in combination with other blood glucose-lowering active ingredients (antidiabetics).

The compounds of the formula I are further suitable for the prevention and treatment of late damage from diabetes, such as, for example, nephropathy, retinopathy, neuropathy and syndrome X, obesity, myocardial infarction, myocardial infarct, peripheral arterial occlusive diseases, thromboses, arteriosclerosis, inflammations, immune diseases, autoimmune diseases such as, for example, AIDS, asthma, osteoporosis, cancer, psoriasis, Alzheimer's, schizophrenia and infectious diseases, preference being given to the treatment of type 1 and type 2 diabetes and for the prevention and treatment of late damage from diabetes, syndrome X and obesity.

Formulations

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. Single-dose formulations which can be administered orally, such as, for example, tablets or capsules, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; in the form of powders or granules; as solution or suspension in an aqueous or nonaqueous liquid; or in the form of an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/ dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Combinations with other medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2003. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are in combination with substances which influence hepatic glucose production, such as, for example, glycogen phosphorylase inhibitors (see: WO 01/94300, WO 02/096864, WO 03/084923, WO 03/084922, WO 03/104188).

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, mefformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in W098/19998, W099/61431, W099/67278, W099/67279, WO01/72290, WO 02/38541, W003/040174, in particular P 93/01 (1-cyclopentyl-3-methyl-1-oxo-2-pentanammonium chloride), P31/98, LAF237 (1-[2-[3-hydroxyadamant-1-ylamino)acetyl]pyrrolidine-2-(S)-carbonitrile), TSO21 ((2S,4S)-4-fluoro-1-[[(2-hydroxy-1,1-dimethylethyl)amino]acetyl]pyrrol idine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in WO 2004/007571, WO 2004/052902, WO 2004/052903.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and mefformin, a sulfonylurea and acarbose, repaglinide and metformin, insulin and a sulfonylurea, insulin and metformin, insulin and troglitazone, insulin and lovastatin, etc.

Lipid modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor see, for example, U.S. Pat. Nos. 6,245,744, 6,221,897, 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, W096/38428, W001/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexyl-methyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6, 7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4- ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethyl-amino]ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g.1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphatamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:

Preparation of brush border membrane vesicles from the small intestine of rabbits, rats and pigs Preparation of brush border membrane vesicles from the intestinal cells of the small intestine was carried out by the so-called $Mg^{2+}$ precipitation method. The mucosa of the small intestine was scraped off and suspended in 60 ml of ice-cold Tris/HCl buffer (pH 7.1)/300 mM mannitol, 5 mM EGTA. Dilution to 300 ml with ice-cold distilled water was followed by homogenization with an Ultraturrax (18 shaft, IKA Werk Staufen, FRG) at 75% of the max. power for 2×1 minute, while cooling in ice. After addition of 3 ml of 1M $MgCl_2$ solution (final concentration 10 mM), the mixture is left to stand at 0° C. for exactly 15 minutes. Addition of $Mg^{2+}$ causes the cell membranes to aggregate and precipitate with the exception of the brush border membranes. After centrifugation at 3000×g (5000 rpm, SS-34 rotor) for 15 minutes, the precipitate is discarded and the supernatant, which contains the brush border membranes, is centrifuged at 26 700×g (15 000 rpm, SS-34 rotor) for 30 minutes. The supernatant is discarded, and the precipitate is rehomogenized in 60 ml of 12 mM Tris/HCl buffer (pH 7.1)/60 mM mannitol, 5 mM EGTA using a Potter Elvejhem homogenizer (Braun, Melsungen, 900 rpm, 10 strokes). Addition of 0.1 ml of 1 M $MgCl_2$ solution and incubation at 0° C. for 15 minutes is followed by centrifugation again at 3000×g for 15 minutes. The supernatant is then centrifuged again at 46 000×g (20 000 rpm, SS-34 rotor) for 30 minutes. The precipitate is taken up in 30 ml of 20 mM Tris/Hepes buffer (pH 7.4)/280 mM mannitol and homogeneously resuspended by 20 strokes in a Potter Elveihem homogenizer at 1000 rpm. After centrifugation at 48 000×g (20 000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended using a tuberculin syringe with a 27 gauge needle. The vesicles were either used directly after preparation for labeling or transport studies or were stored at −196° C. in 4 mg portions in liquid nitrogen. To prepare brush border membrane vesicles from rat small intestine, 6 to 10 male Wistar rats (bred at Kastengrund, Aventis Pharma) were sacrificed by cervical dislocation, and the small intestines were removed and rinsed with cold isotonic saline. The intestines were cut up and the mucosa was scraped off. The processing to isolate brush border membranes took place as described above. To remove cytoskeletal fractions, the brush border membrane vesicles from rat small intestine were treated with KSCN as chaotropic ion.

To prepare brush border membranes from rabbit small intestine, rabbits were sacrificed by intravenous injection of 0.5 ml of an aqueous solution of 2.5 mg of tetracaine HCl, 100 mg of m-butramide and 25 mg of mebezonium iodide. The small intestines were removed, rinsed with ice-cold physiological saline and stored frozen in plastic bags under nitrogen at −80° C. and 4 to 12 weeks. For preparation of the membrane vesicles, the frozen intestines were thawed at 30° C. in a water bath and then the mucosa was scraped off. Processing to give membrane vesicles took place as described above.

To prepare brush border membrane vesicles from pig intestine, jejunum segments from a freshly slaughtered pig were rinsed with ice-cold isotonic saline and frozen in plastic bags under nitrogen at −80° C. Preparation of the membrane vesicles took place as described above.

Measurement of the glucose uptake by brush border membrane vesicles

The uptake of [$^{14}$C]-labeled glucose into brush border membrane vesicles was measured by the membrane filtration method. 10 μl of the brush border membrane vesicle suspension in 10 mM Tris/Hepes buffer (pH 7.4)/300 mM mannitol were added at 20° C. to 90 μl of a solution of 10 pM [$^{14}$C]D glucose and the appropriate concentrations of the relevant inhibitors (5-200 µM) in 10 mM Tris/Hepes buffer (pH 7.4)/100 mM NaCl/100 mM.

After incubation for 15 seconds, the transport process was stopped by adding 1 ml of ice-cold stop solution (10 mM Tris/Hepes buffer (pH 7.4)/150 mM KCl) and the vesicle suspension was immediately filtered with suction through a cellulose nitrate membrane filter (0.45 µm, 25 mm diameter, Schleicher & Schüll) under a vacuum of from 25 to 35 mbar. The filter was washed with 5 ml of ice-cold stop solution. Each measurement was carried out as duplicate or triplicate determination. To measure the uptake of radiolabeled substrates, the membrane filter was dissolved in 4 ml of an appropriate scintillator (Quickszint 361, Zinsser Analytik GmbH, Frankfurt am Main), and the radioactivity was determined by liquid scintillation measurement. The measured values were obtained as dpm (decompositions per minute) after calibration of the instrument using standard samples and after correction for any chemiluminescence present.

The active ingredients are compared for activity on the basis of $IC_{50}$ data obtained in the transport assay on rabbit small intestine brush border membrane vesicles for selected substances. (The absolute values may be species- and experiment-dependent).

A further method for testing the activity of the compounds is the inhibition of the transport activity of the human sodium-dependent glucose transporter 1 (SGLT1, SLC5A1) in vitro:

1. Cloning of an Expression Vector for Human SGLT1

The cDNA for human SGLT1 was introduced into the pcDNA4/TO vector (Invitrogen) by standard methods of molecular biology as described in Sambrook et al. (Sambrook et al., Molecular Cloning, A Laboratory Manual, 2nd Edition). The subsequent sequencing of the insert revealed complete identity with bases 11 to 2005 of the base sequence for human SGLT1 which was described by Hediger et al. (Hediger et al., *Proc. Natl. Acad. Sci. USA* 1989, 86, 5748-5752.) and deposited in the GenBank sequence database (GenBank Accesion Number: M24847). Bases 11 to 2005 correspond to the complete coding region of human SGLT1.

2. Preparation of a Recombinant Cell Line with Inducible Expression of Human SGLT1

The expression vector for human SGLT1 was introduced into CHO-TRex cells (Invitrogen) by means of FuGene6 lipofection (Roche). To select single cell clones, 600 µg/ml Zeocin (Invitrogen) was added to the cell culture medium (Nutrient Mixture F-12 (Ham), (Invitrogen) supplemented with 10% fetal calf serum (BD Biosciences), 10 µg/ml blasticidin S (CN Biosciences), 100 units/ml penicillin, 100 units/ml streptomycin). The functionality of the single cell clones resulting from the selection was tested via their uptake activity for radiolabeled methyl α-D-glucopyranoside. The cell clone with the greatest uptake activity for methyl α-D-glucopyranoside, referred to as CHO-TRex-hSGLT1 hereinafter, was selected for further experiment, and cultivation was continued in the presence of 600 µg/ml of zeocin.

3. Measurement of the Inhibitory Effect of Test Substances on the Uptake of Methyl □-D-glucopyranoside (□-MDG)

CHO-TRex-hSGLT1 cells were seeded in a concentration of 50 000 cells per well in Cytostar-T scintillating 96-well plates (Amersham Biosciences) in cell culture medium and cultivated for 24 h. Expression of the recombinant human SGLT1 was induced by adding 1 pg/ml tetracyclin for a further 24 h. For α-MDG uptake experiments, the cells were washed with PBS and then starved (PBS supplemented with 10% fetal calf serum) at 37° C. for one hour. After a further washing step with transport assay buffer (140 mM sodium chloride, 2 mM potassium chloride, 1 mM magnesium chloride, 1 mM calcium chloride, 10 mM HEPES/Tris, pH 7.5), the cells were incubated either in the absence or presence of test substances varying in concentration at room temperature for 15 min. The test substances were diluted appropriately in transport assay buffer (40 µl/well) starting from a 10 mM stock solution in dimethyl sulfoxide.

The assay was then started by adding 10 µl of a mixture of radiolabeled methyl α-D-[U-$^{14}$C]glucopyranoside (Amersham) and unlabeled methyl α-D-glucopyranoside (Acros). The final concentration of methyl α-D-glucopyranoside in the assay was 50 µM. After an incubation time of 30 min at room temperature, the reaction was stopped by adding 50 82 l/well of 10 mM methyl α-D-glucopyranoside in transport assay buffer (4° C.), and the radioactivity uptake by the cells was determined in a MicroBeta Scintillation Microplate Reader (Wallac). The half-maximum inhibitory effect of the test substances (IC50) was determined in the following way:

1. Establishment of the value for 0% inhibition. This is the measurement in the absence of substance, measured in sodium-containing transport assay buffer.
2. Establishment of the value for 100% inhibition. This is the measurement in the absence of substance, measured in sodium-free transport assay buffer (140 mM choline chloride, 2 mM potassium chloride, 1 mM magnesium chloride, 1 mM calcium chloride, 10mM HEPES/Tris, pH7.5).
3. Calculation of the percentage inhibitions for the measurements carried out in the presence of various concentrations of test substance. It was then possible to ascertain therefrom the concentration of test substance which reduced the uptake of methyl α-D-glucopyranoside by 50% (IC50).

IC50 values of test substances (µM) [in vitro testing of the uptake of methyl α-D-glucopyranoside]

| Example No. | $IC_{50}$ [µM] |
| --- | --- |
| 3 | 0.043 |
| 6 | 0.133 |
| 9 | 0.081 |
| 12 | 0.139 |
| 15 | 0.170 |
| 18 | 0.080 |
| 21 | 0.047 |
| 22 | 0.144 |
| 24 | 0.208 |
| 31 | 0.252 |
| 33 | 0.070 |
| 36 | 0.043 |

The examples detailed below serve to illustrate the invention without, however, restricting it.

TABLE 1

Compounds of the formula I

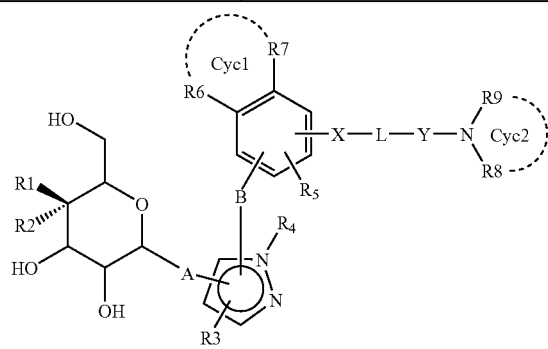

| Ex. | R1 | R2 | R3 | R4 | R5 | R6 | R7 | R8, R9 | A | B | X | L | Y | MS* | $t_R$ [min] |
|---|---|---|---|---|---|---|---|---|---|---|---|---|---|---|---|
| 1 | H | F | i-Pr | H | H | H | H | CH₂CH₂NHCH₂CH₂ | O | CH₂ | — | —CH=CH— | — | 505.47 | 1.19 |
| 2 | H | F | i-Pr | H | H | H | H | H; CH₂CH₂CH₂CH₃ | O | CH₂ | — | —CH₂CH₂CH₂— | CO | 522.57 | 1.74 |
| 3 | H | F | i-Pr | H | H | H | H | H; CH₂CH₂CONH₂ | O | CH₂ | — | —CH=CHCH₂— | CO | 535.44 | 1.15 |
| 4 | H | F | i-Pr | H | H | H | H | H; CH₂CH₂CONH₂ | O | CH₂ | — | —CH₂CH₂CH₂— | CO | 537.44 | 1.13 |
| 5 | H | F | i-Pr | H | H | H | H | H; CH₂CONH₂ | O | CH₂ | — | —CH₂CH₂CH₂— | CO | 523.38 | 1.15 |
| 6 | H | F | CH₃ | H | H | H | H | H; CH₂CH₂CONH₂ | O | CH₂ | — | —CH₂CH₂CH₂— | CO | 509.33 | 1.02 |
| 7 | H | F | i-Pr | H | H | H | H | H; CH₂CH₂CONH₂ | O | CH₂ | — | —CH₂CH₂— | CO | 523.42 | 1.36 |
| 8 | H | F | i-Pr | H | H | H | H | H; CH₂CONH₂ | O | CH₂ | — | —CH₂CH₂— | CO | 509.29 | 1.08 |
| 9 | H | F | i-Pr | H | H | H | H | H; CH[CH₂OH]CONH₂ | O | CH₂ | — | —CH₂CH₂CH₂— | CO | 552.29 | 1.13 |
| 10 | H | F | CH₃ | H | H | H | H | H; CH[CH₂OH]CONH₂ | O | CH₂ | — | —CH₂CH₂CH₂— | CO | 523.31 | 1.02 |
| 11 | H | F | CH₃ | H | H | H | H | CH₂CH₂N[CH₂CH₂OH]CH₂CH₂ | O | CH₂ | — | —CH₂CH₂CH₂— | CO | 551.30 | 0.95 |
| 12 | H | F | i-Pr | H | H | H | H | CH₂CH₂N[CH₃]CH₂CH₂ | O | CH₂ | — | —CH₂CH₂CH₂— | CO | 549.30 | 1.07 |
| 13 | H | F | i-Pr | H | H | H | H | CH₂CH₂CH₂CH₂CH₂ | O | CH₂ | — | —CH₂CH₂CH₂— | CO | 534.54 | 1.77 |
| 14 | H | F | i-Pr | H | H | H | H | CH₂CH₂CH₂CH₂CH₂CH₂ | O | CH₂ | — | —CH₂CH₂CH₂— | CO | 538.56 | 1.83 |
| 15 | H | F | i-Pr | H | H | H | H | CH₂CH₂CH₂CH₂ | O | CH₂ | — | —CH₂CH₂CH₂— | CO | 520.52 | 1.67 |
| 16 | H | F | i-Pr | H | H | H | H | CH₂CH₂NHCH₂CH₂ | O | CH₂ | — | —CH₂CH₂CH₂— | CO | 535.32 | 1.06 |
| 17 | H | F | i-Pr | H | H | H | H | H; CH₂CH₂OH | O | CH₂ | — | —CH₂CH₂— | CO | 496.34 | 1.37 |
| 18 | H | F | i-Pr | H | H | H | H | H; C[CH₃]₂CH₂OH | O | CH₂ | — | —CH₂CH₂— | CO | 524.26 | 1.34 |
| 19 | H | F | i-Pr | H | H | H | H | H; C[CH₃]₂CH₂OH | O | CH₂ | — | —CH₂CH₂CH₂— | CO | 538.28 | 1.26 |
| 20 | H | F | i-Pr | H | H | H | H | H; CH₂CH₂OH | O | CH₂ | — | —CH=CH— | CO | 494.28 | 1.10 |
| 21 | H | F | i-Pr | H | H | H | H | H; C[CH₂OH]₃ | O | CH₂ | — | —CH₂CH₂CH₂— | CO | 570.33 | 1.14 |
| 22 | H | F | i-Pr | H | H | H | H | H; CH₂CH₂CH₂NH₂ | O | CH₂ | — | —CH₂CH₂CH₂— | CO | 522.52 | 1.74 |
| 23 | H | F | i-Pr | H | H | H | H | H; CH₂-adamantyl | O | CH₂ | — | CH₂CH₂CH₂— | CO | 614.45 | 2.11 |
| 24 | H | F | i-Pr | H | H | H | H | H; tetrahydropyran(OH)₃CH₂OH | O | CH₂ | — | CH₂CH₂CH₂— | CO | 628.25 | 1.07 |
| 25 | H | F | i-Pr | H | H | H | H | CH₂CH₂N[SO₃H]CH₂CH₂ | O | CH₂ | — | CH₂CH₂CH₂— | CO | 615.42 | 1.64 |
| 26 | H | F | i-Pr | H | H | H | H | H; CH₂CH₂CH₂NHSO₃H | O | CH₂ | — | CH₂CH₂CH₂— | CO | 603.41 | 1.56 |
| 27 | H | F | i-Pr | H | H | H | H | H; CH₂CH₂OSO₃H | O | CH₂ | — | CH₂CH₂CH₂— | CO | 588.50 | 1.60 |
| 28 | H | F | i-Pr | H | H | H | H | H; C[CH₃]₂CH₂OSO₃H | O | CH₂ | — | CH₂CH₂CH₂— | CO | 616.52 | 1.61 |
| 29 | H | F | i-Pr | H | H | H | H | CH₂CH₂OCH₂CH₂ | O | CH₂ | — | —CH₂CH₂CH₂— | CO | 536.48 | 1.58 |
| 30 | H | F | i-Pr | H | H | H | H | H; C[CH₃]₂CH₂CH₃ | O | CH₂ | — | —CH₂CH₂CH₂— | CO | 536.54 | 1.84 |
| 31 | H | F | CH₃ | H | H | H | H | H; CH₂CH₂CH₃ | O | CH₂ | — | —CH₂CH₂CH₂— | NHCO | 494.12 | 2.77 |
| 32 | H | F | i-Pr | H | H | H | H | H; H | O | CH₂ | CO | —NHCH₂CH₂— | — | 494.97 | 0.97 |
| 33 | H | F | i-Pr | H | H | H | H | H; H | O | CH₂ | CO | —NHCH₂— | — | 481.19 | 1.02 |
| 34 | H | F | CF₃ | H | H | H | H | H; H | O | CH₂ | CO | —NHCH₂CH₂— | — | 521.16 | 1.00 |
| 35 | H | F | CF₃ | H | H | H | H | H; H | O | CH₂ | CO | —NHCH₂— | — | 507.16 | 1.20 |
| 36 | H | F | i-Pr | H | H | H | H | CH₂CH₂N[CH₃]CH₂CH₂ | O | CH₂ | — | —CH₂CH₂CH₂— | NHCO | n.d. | n.d. |
| 37 | H | F | i-Pr | H | H | H | H | H; C[CH₃]₂CH₂OH | O | CH₂ | — | —CH₂CH₂CH₂— | NHCO | n.d. | n.d. |

The linkages are indicated in the description of the examples in the experimental section.

Gradient for LCMS: aceronitrile+0.05% TFA: 5:95 ( min) to 95:5(2.3 min) to 95:5(3 min);column:YMC J'shere 33×4 M, 1.3 mL/min flow (gradient 1)

Further LCMS gradients differing therefrom are indicated in the experimental section:

Gradient 2: 0 min 96% $H_2O$ (0.05% TFA) to 2.0 min-95% MeCN, then to 2.4 min 95% MeCN; then to 4% MeCN by 2.45 min.; 1 mL/min; 110-1000 MW; 0.4 L (YMC J'sphere ODS H80 20×2 1.4

Gradient 3: 0 min 95%$H_2O$ (5 mmol ammonium acetate) to 3.5 min at 95% MeCN, then for 2 min 95% ACN; then in one minute to 5% MeCN; 0.5 mL/min; 115-1000 MW; 1 L (Merck Purospher 3, 2×55 mm), The invention further relates to processes for preparing the compounds of the general formula I.

The preparation of the examples is described in detail below. The compounds of the invention can be obtained analogously or in accordance with the processes described in WO 0414932 and WO 0418491.

EXPERIMENTAL SECTION

Reaction scheme: Synthesis of the -bromoglycoside 4

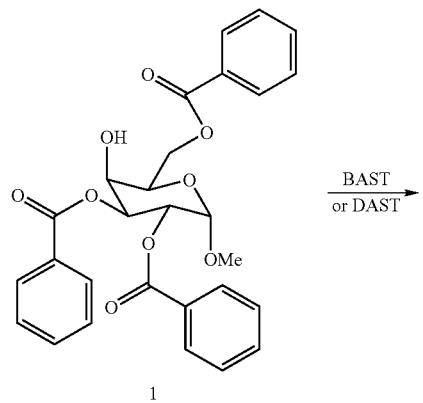

1

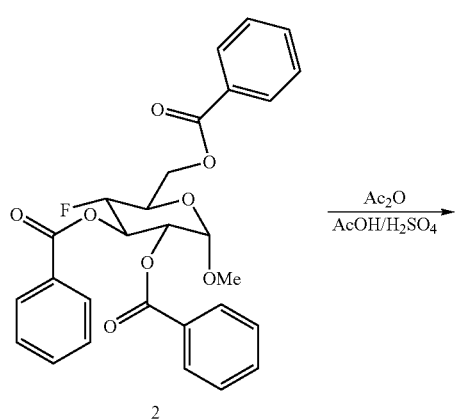

2

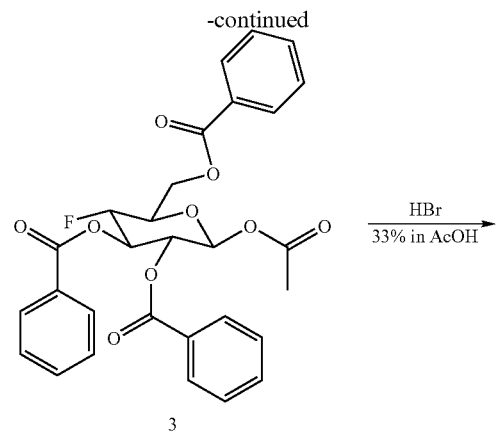

3

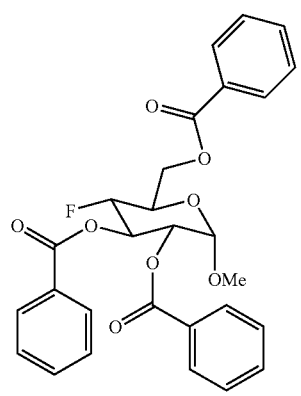

4

Methyl 2,3,6-tri-O-benzoyl-4-fluoro-4-deoxy-☐-D-gl ucopyranoside (2)

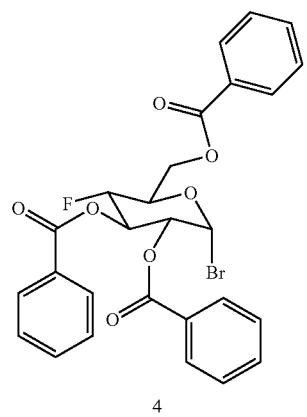

2

3.0 g of methyl 2,3,6-tri-O-benzoyl-☐-D-galactopyranoside (Reist et al., J. Org. Chem 1965, 30, 2312) are introduced into dichloromethane and cooled to −30° C. Then 3.06 ml of [bis(2-methoxyethyl)amino]sulfur trifluoride (BAST) are added dropwise. The reaction solution is warmed to room temperature and stirred for 12 h. The mixture is diluted with dichloromethane, and the organic phase is extracted with $H_2O$, $NaHCO_3$ solution and saturated NaCl solution. The organic phase is dried over $Na_2SO_4$ and concentrated. The crude product is crystallized from ethyl acetate and heptane.

1.95 g of the product 2 are obtained as a colorless solid. $C_{28}H_{25}FO_8$ (508.51) MS (ESI$^+$) 526.18 (M+NH$_4^+$). Alternatively, the reaction can also be carried out using 2.8 eq. of diethylaminosulfur trifluoride (DAST); in this case, the reaction solution is refluxed for 18 h after the addition. The working up takes place in analogy to the above description.

1-O-Acetyl-2,3,6-tri-O-benzoyl-4-fluoro-4-deoxy-glucose (3)

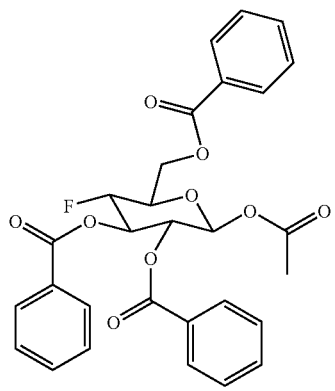

3

12.0 g of compound methyl 2,3,6-tri-O-benzoyl-4-fluoro-4-deoxy-☐-D-glucopyranoside are suspended in 150 ml of acetic anhydride. 8.4 ml of conc. sulfuric acid are mixed with 150 ml of glacial acetic acid and added to the mixture while cooling in ice. The mixture stirs at room temperature for 60 h. The mixture is poured into NaHCO$_3$ solution, and this solution is extracted with dichloromethane. The organic phase is extracted with NaCl solution, dried with Na$_2$SO$_4$ and concentrated. The residue is recrystallized from ethyl acetate/heptane. 5.97 g of the product 3 are obtained as a colorless solid. $C_{29}H_{25}FO_9$ (536.52) MS (ESI$^+$) 554.15 (M+NH$_4^+$)

1-Bromo-4-deoxy-4-fluoro-2,3,6-tri-O-benzoyl-alpha-D-glucose (4)

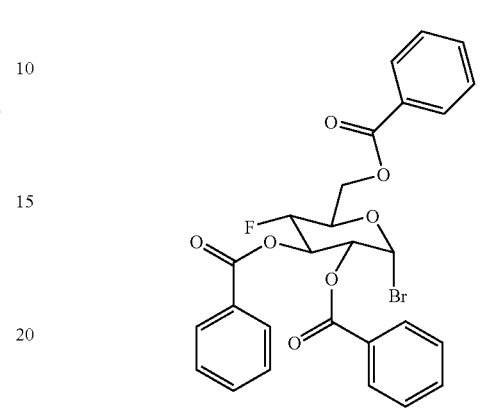

4

1.44 g of 1-O-acetyl-2,3,6-tri-O-benzoyl-4-fluoro-4-deoxyglucose are dissolved in 20 ml of hydrobromic acid in glacial acetic acid (33%) and stirred at room temperature. After 5 hours, the mixture is poured into ice-water, and the aqueous phase is extracted three times with dichloromethane. The collected organic phase is washed with saturated sodium chloride solution, dried over sodium sulfate and evaporated to dryness. The crude product is filtered through a silica gel column with ethyl acetate/heptane 70:30. 1.40 g of the product 4 are obtained as a colorless solid. $C_{27}H_{22}BrFO_7$ (557.37) MS (ESI$^+$) 574.05/576.05 (M+NH$_4^+$)

Reaction Scheme I: Synthesis of Example 1

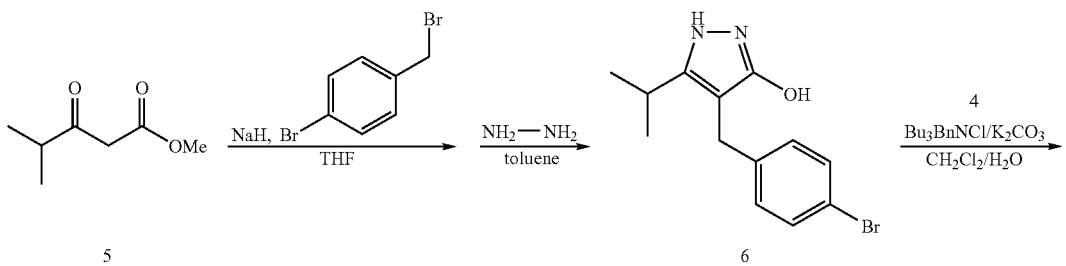

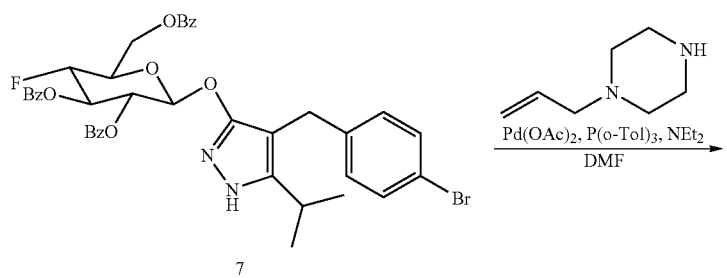

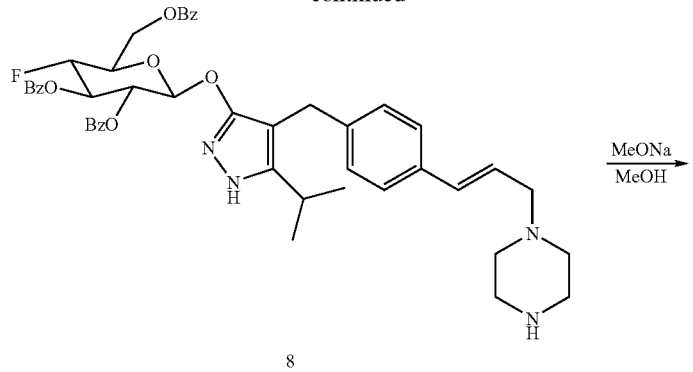

8

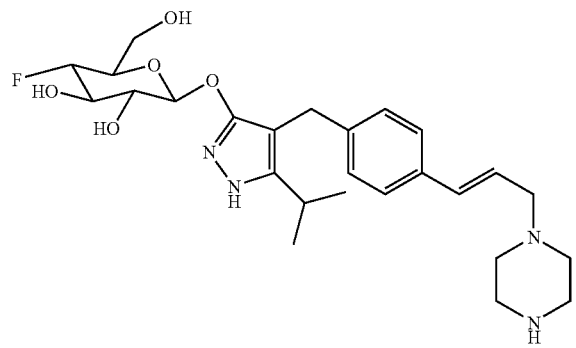

9 (Example 1)

4-(4-Bromobenzyl)-5-isopropylpyraz-3-ol (6)

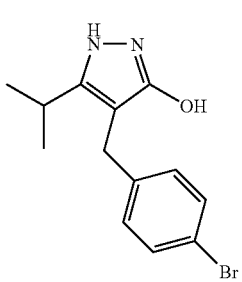

6

Compound 7

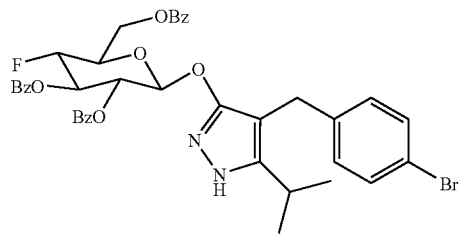

7

15.2 g of methyl isobutyrylacetate (5) are added to a suspension of sodium hydride (60%, 3.85 g) in 250 ml of tetrahydrofuran while cooling in ice. A solution of 20.0 g of 4-bromobenzyl bromide in 100 ml of THF is then added and the mixture is stirred at room temperature for 48 h. After addition of 300 ml of H$_2$O and 300 ml of EtOAc, the organic phase is dried over MgSO$_4$ and the solvent is stripped off in a rotary evaporator. The resulting crude product is dissolved in 120 ml of toluene, mixed with hydrazine hydrate (8.01 g) and heated under reflux with a water trap for 12 h. The reaction mixture is concentrated to a volume of 50 ml and cooled to 0° C. of the crystallized product is filtered off with suction and washed with heptane. 10.8 g of the compound 6 are obtained as a pale yellow solid.

C$_{13}$H$_{15}$BrN$_2$O (295.18) MS (ESI$^+$294.04 (M+H$^+$).

530 mg of 4-(4-bromobenzyl)-5-isopropylpyraz-3-ol (6) and 1.50 g of bromide 4 are dissolved in 50 ml of methylene chloride. To this solution are successively added 1.86 g of potassium carbonate, 91 mg of benzyl-triethylammonium bromide and 0.8 ml of water, and it is then stirred at room temperature for 24 hours. The reaction solution is transferred into a separating funnel and washed successively with water and saturated sodium chloride solution. The organic phase is dried over magnesium sulfate and concentrated in a rotary evaporator. The crude product is separated by chromatography on silica gel (EtOAc/heptane). 193 mg of 7 are obtained as a colorless solid. C$_{40}$H$_{36}$BrFN$_2$O$_8$ (771.6) MS (ESI$^+$) 773.1 (M+H$^+$).

Compound 8

Compound 9 (Example 1)

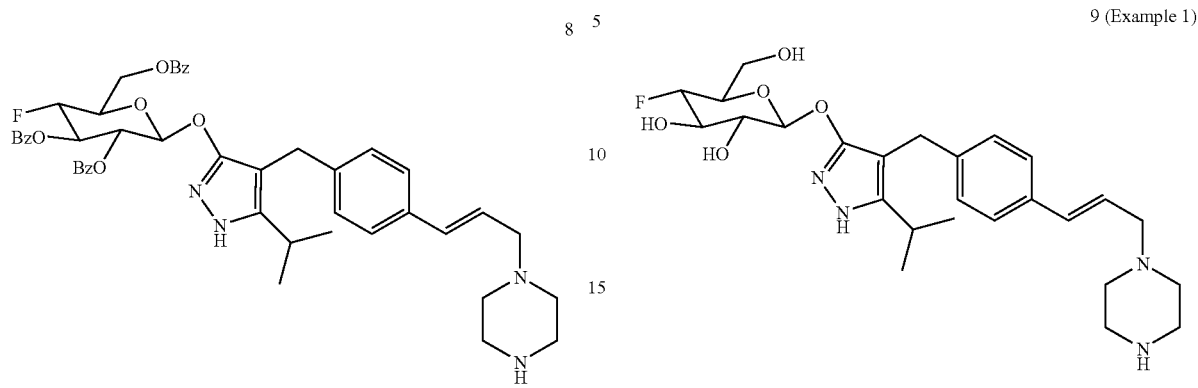

193 mg of the glycoside 7 are dissolved in 1.25 ml of DMF, and 2.3 mg of Pd(OAc)$_2$, 6.09 mg of tri-o-tolylphosphine, 0.25 ml of triethylamine and 84.6 ml of 1-allylpiperazine are added. The reaction mixture is heated in an oil bath at 100° C. for 18 h. The solvent is removed in a rotary evaporator, and the crude product is purified by chromatography on silica gel (EtOAc/MeOH). 117 mg of the compound 8 are obtained as a colorless wax. C$_{47}$H$_{49}$FN$_4$O$_8$ (816.9) MS (ESI$^+$) 817.05 (M+H$^+$).

98 mg of the glycoside 8 are taken up in 4 ml of a mixture of methanol/water/triethylamine (3:3:1) and stirred at room temperature for 48 h. The reaction mixture is concentrated in a rotary evaporator, and the residue is purified by chromatography on silica gel (methylene chloride/methanol/conc. ammonia). 34 mg of the compound 9 are obtained as a colorless solid. C$_{26}$H$_{37}$FN$_4$O$_5$ (504.61) MS (ESI$^+$) 505.47 (M+H$^+$).

Reaction Scheme II: Synthesis of Example 2

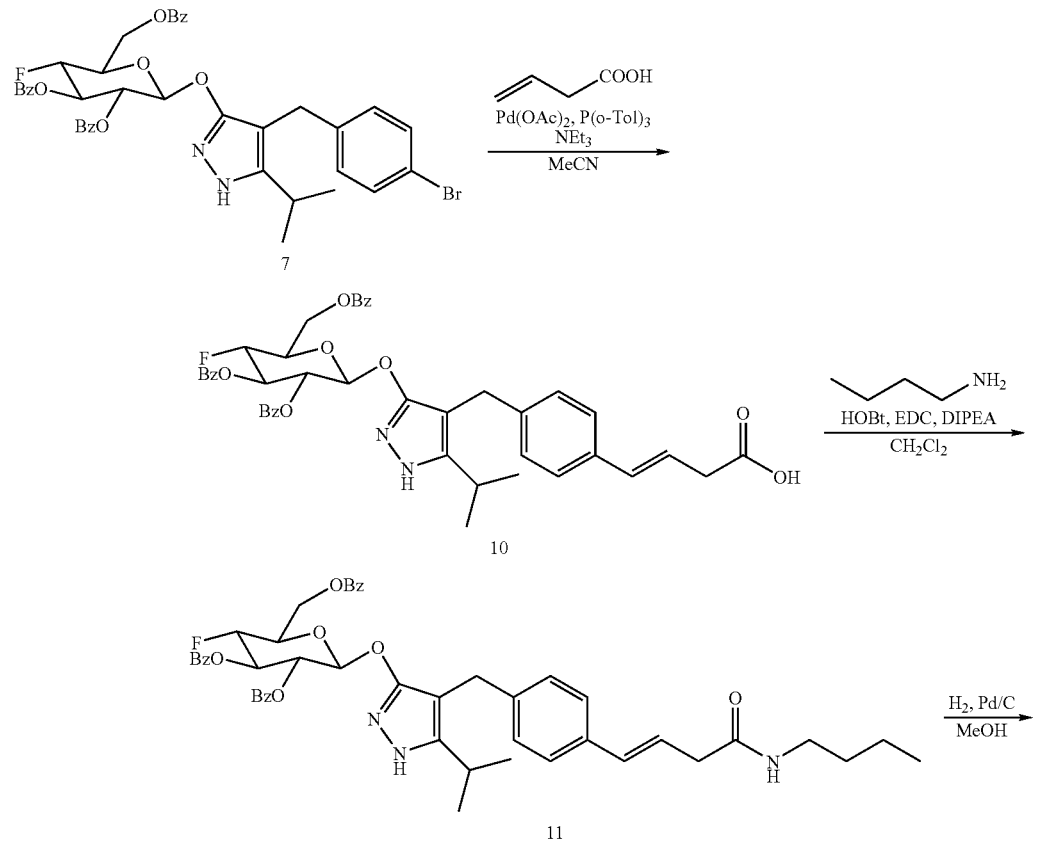

-continued

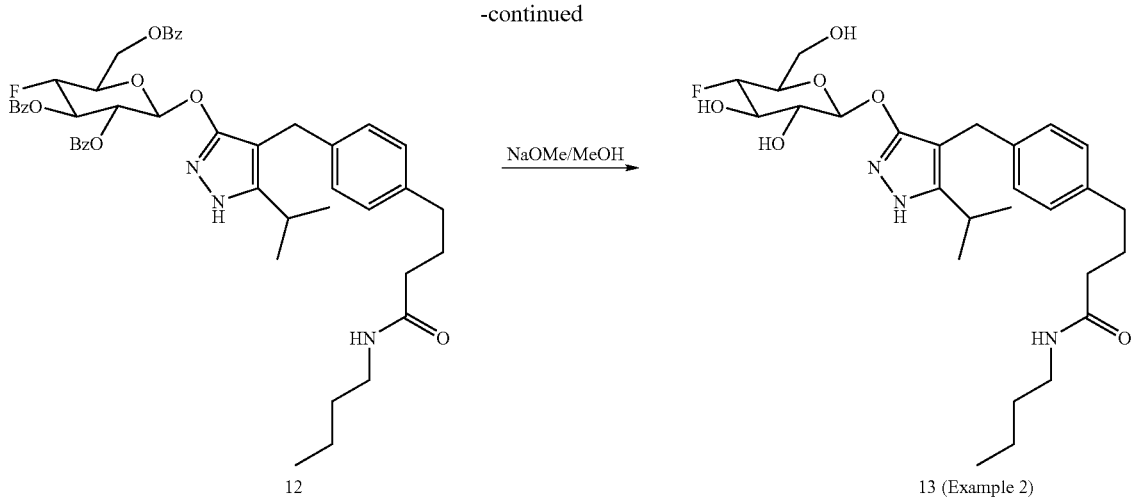

Compound 10

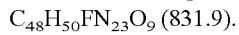

7.20 g of the glycoside 7 are dissolved in 109 ml of acetonitrile, and 41.9 mg of Pd(OAc)$_2$, 113.6 mg of tri-o-tolylphosphine, 39.2 ml of triethylamine and 1.04 g of vinyl acetic acid are added. The reaction mixture is heated under reflux for 60 h. The solvent is removed in a rotary evaporator, and the crude product is purified by chromatography on silica gel (CH$_2$Cl$_2$/MeOH/conc. ammonia=30/5/1). 6.18 g of the compound 10 are obtained as a colorless wax. C$_{44}$H$_{41}$FN$_2$O$_{10}$ (776.8).

Compound 11

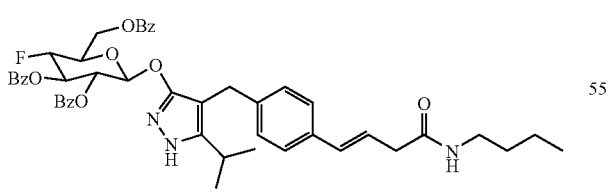

100 mg of compound 10 are dissolved in 4.00 ml of dichloromethane, and 9.41 mg of n-butylamine, 119.8 mg of diisopropylethylamine, 26.1 mg of 1-hydroxybenzotriazole and 30 mg of N-(3-dimethylaminopropyl)-N-ethylcarbodiimide are added. The reaction mixture is stirred at 20° C. for 16 h. The solution is washed successively with in each case 5 ml of NaHCO$_3$ solution, 5 ml of 0.2M hydrochloric acid and 5 ml of saturated NaCl solution. The solvent is removed in a rotary evaporator, and the crude product is converted without further purification into compound 12.
C$_{48}$H$_{50}$FN$_{23}$O$_9$ (831.9).

Compound 12

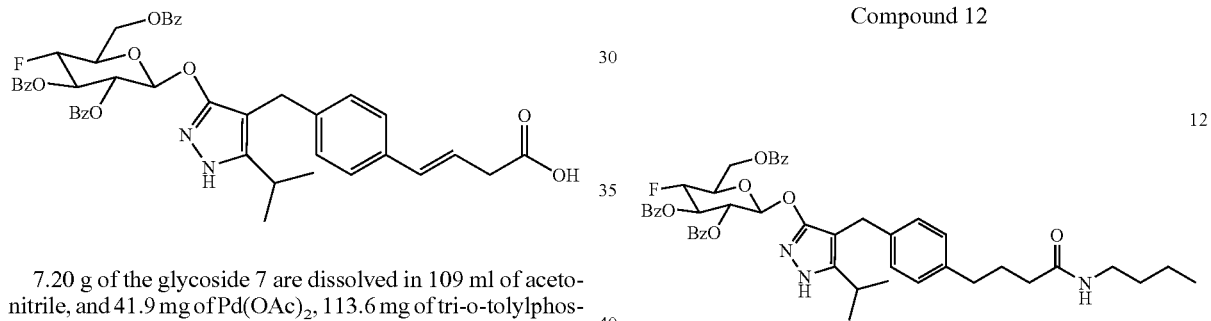

82 mg of compound 11 are dissolved in 5.00 ml of methanol, and 10.5 mg of palladium on activated carbon (10%) are added. The reaction mixture is stirred under an atmosphere of 1 bar of H$_2$ for 16 h. Palladium on carbon is filtered off, and the solvent is removed in a rotary evaporator. Further purification of the crude product on silica gel is unnecessary. 72 mg of the desired compound 12 are obtained as a colorless wax. C$_{48}$H$_{52}$FN$_{23}$O$_9$ (834.0).

Compound 13 (Example 2)

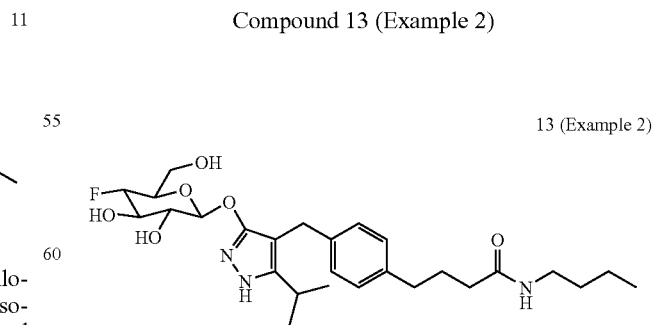

72 mg of the glycoside 12 are dissolved in 10 ml of methanol, and 1.72 ml of a 2M methanolic sodium methoxide solution are added. The reaction mixture is stirred at 20° C.

for 4 h, and 46.2 mg of ammonium chloride are added. The solvent is removed in a rotary evaporator, and the crude product is purified on silica gel (initially with ethyl acetate/heptane=5/1; subsequently methylene chloride/methanol/conc. ammonia=30/5/1). 24 mg of the compound 13 are obtained as a colorless solid. $C_{27}H_{40}FN_3O_9$ (521.63): MS (ESI$^+$) 522.57 (M+H$^+$).

Compound 14 (Example 3)

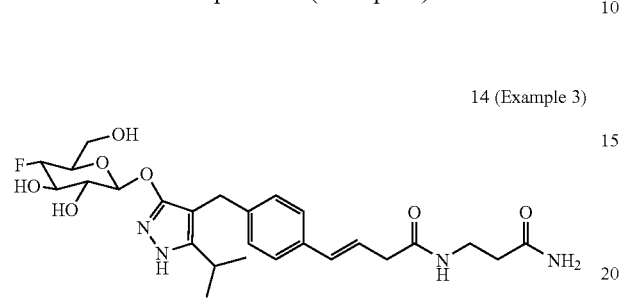

14 (Example 3)

Compound 14 is synthesized in analogy to the synthesis route described for compound 13 (example 2). Starting from the glycoside 10, which is, however, reacted not with n-butylamine but with 3-aminopropionamide hydrochloride, and without carrying out the subsequent hydrogenation, compound 14 is obtained as a colorless solid. $C_{26}H_{35}FN_4O_7$ (534.6): MS (ESI$^+$) 535.44 (M+H$^+$).

Compound 15 (Example 4)

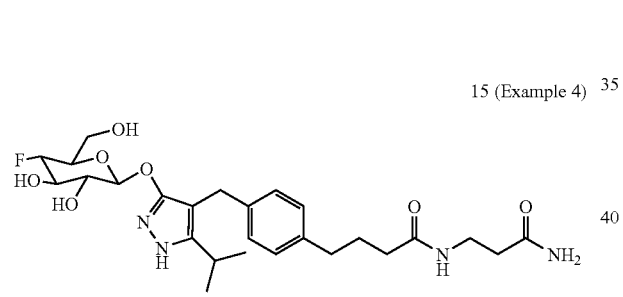

15 (Example 4)

Compound 15 is synthesized in analogy to the synthesis route described for compound 13 (example 2). Starting from the glycoside 10, which is, however, reacted not with n-butylamine but with 3-aminopropionamide hydrochloride, compound 15 is obtained as a colorless solid. $C_{26}H_{37}FN_4O_7$ (536.6): MS (ESI$^+$) 537.44 (M+H$^+$).

Compound 16 (Example 5)

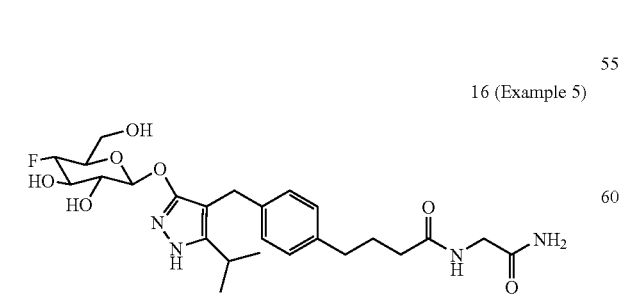

16 (Example 5)

Compound 16 is synthesized in analogy to the synthesis route described for compound 13 (example 2). Starting from the glycoside 10, which is, however, reacted not with n-butylamine but with glycinamide hydrochloride, compound 16 is obtained as a colorless wax.

$C_{25}H_{35}FN_4O_7$ (522.6): MS (ESI$^+$) 523.38 (M+H$^+$).

Compound 17

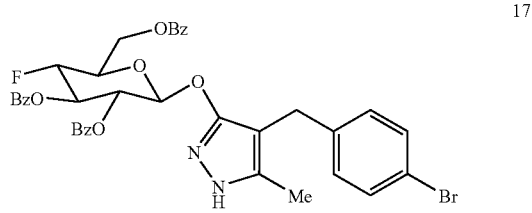

17

Compound 17 is synthesized in analogy to the synthesis route described for compound 7 (scheme 1). However, ethyl acetoacetate is used as starting material instead of methyl isobutyrylacetate. Compound 17 is obtained as a colorless solid. $C_{38}H_{32}BrFN_2O_8$ (743.6).

Compound 18 (Example 6)

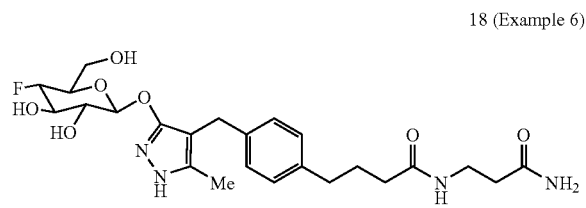

18 (Example 6)

Compound 18 is synthesized in analogy to the synthesis described for compound 15 (example 4). However, the glycoside 17 is used as starting material instead of glycoside 10. Compound 18 is obtained as a colorless wax.

$C_{24}H_{33}FN_4O_7$ (508.6): MS (ESI$^+$) 509.33 (M+H$^+$).

Compound 19 (Example 7)

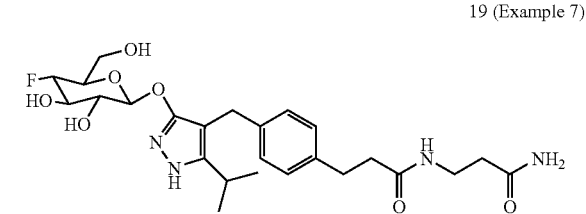

19 (Example 7)

Compound 19 is synthesized in analogy to the synthesis described for compound 15 (example 4). However, the bromo compound 7 is reacted with acrylic acid instead of vinylacetic acid. Compound 19 is obtained as a colorless wax. $C_{25}H_{35}FN_4O_7$ (522.6): MS (ESI$^+$) 523.42 (M+H$^+$).

Compound 20 (Example 8)

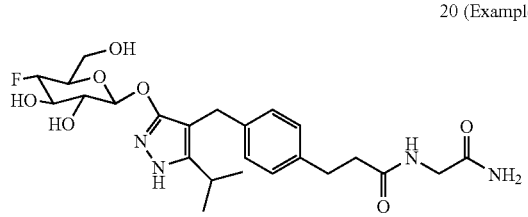

20 (Example 8)

Compound 20 is synthesized in analogy to the synthesis described for compound 19 (example 7). However, 3-aminopropionamide hydrochloride is replaced by glycinamide hydrochloride in the amide coupling. Compound 20 is obtained as a colorless wax. $C_{24}H_{33}FN_4O_7$ (508.6): MS (ESI$^+$) 509.29 (M+H$^+$).

Compound 21 (Example 9)

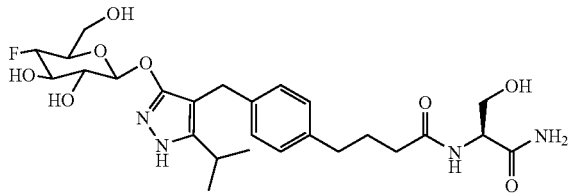

21 (Example 9)

Compound 21 is synthesized in analogy to the synthesis route described for compound 13 (example 2). Starting from the glycoside 10, which is, however, reacted not with n-butylamine but with L-serinamide hydrochloride, compound 21 is obtained as a colorless solid. $C_{26}H_{37}FN_4O_8$ (552.6): MS (ESI$^+$) 553.29 (M+H$^+$).

Compound 22 (Example 10)

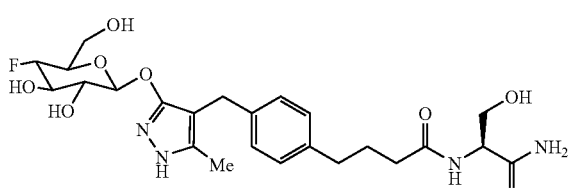

22 (Example 10)

Compound 22 is synthesized in analogy to the synthesis described for compound 18 (example 6). Starting from the glycoside 17, which is, however, reacted not with 3-aminopropionamide hydrochloride but with L-serinamide hydrochloride, compound 22 is obtained as a colorless wax.

$C_{24}H_{33}FN_4O_8$ (524.6): MS (ESI$^+$) 525.31 (M+H$^+$).

Compound 23 (Example 11)

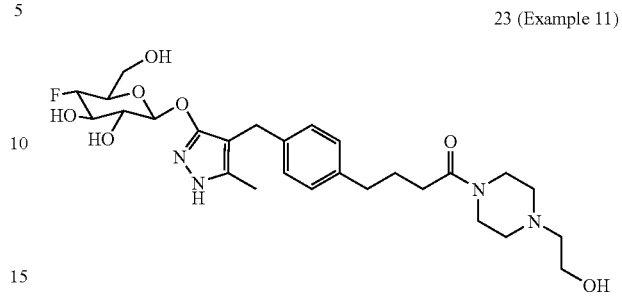

23 (Example 11)

Compound 23 is synthesized in analogy to the synthesis route described for compound 18 (example 6). Starting from the glycoside 17, which is, however, reacted not with 3-aminopropionamide hydrochloride but with N-(2-hydroxyethyl)piperazine, compound 23 is obtained as a colorless wax.

$C_{27}H_{39}FN_4O_7$ (550.6): MS (ESI$^+$) 551.30 (M+H$^+$).

Compound 24 (Example 12)

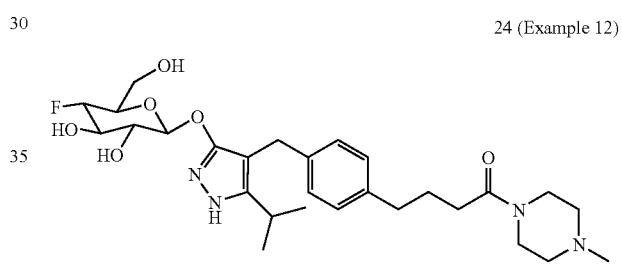

24 (Example 12)

Compound 24 is synthesized in analogy to the synthesis route described for compound 13 (example 2). Starting from the glycoside 10, which is, however, reacted not with n-butylamine but with N-methylpiperazine, compound 24 is obtained as a colorless wax. $C_{28}H_{41}FN_4O_6$ (548.7): MS (ESI$^+$) 549.30 (M+H$^+$).

Compound 25 (Example 13)

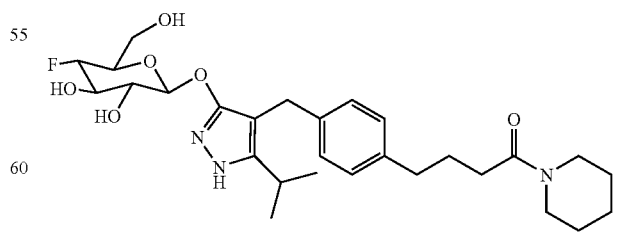

25 (Example 13)

Compound 25 is synthesized in analogy to the synthesis route described for compound 13 (example 2). Starting from the glycoside 10, which is, however, reacted not with n-butylamine but with piperidine, compound 25 is obtained as a colorless wax. $C_{28}H_{40}FN_3O_6$ (533.7): MS (ESI$^+$) 534.54 (M+H$^+$).

Compound 26 (Example 14)

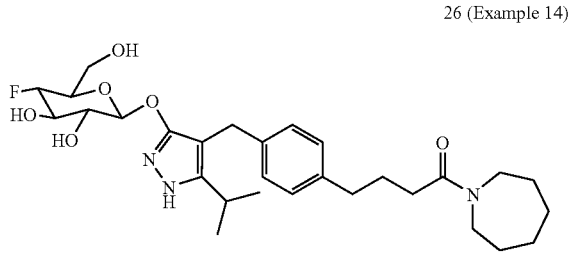

26 (Example 14)

Compound 26 is synthesized in analogy to the synthesis route described for compound 13 (example 2). Starting from the glycoside 10, which is, however, reacted not with n-butylamine but with hexahydro-1H-azepine, compound 26 is obtained as a colorless wax.

$C_{29}H_{42}FN_3O_6$ (547.7): MS (ESI$^+$) 548.56 (M+H$^+$).

Compound 27 (Example 15)

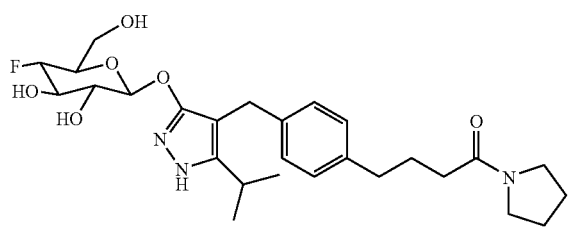

27 (Example 15)

Compound 27 is synthesized in analogy to the synthesis route described for compound 13 (example 2). Starting from the glycoside 10, which is, however, reacted not with n-butylamine but with pyrrolidine, compound 27 is obtained as a colorless wax. $C_{27}H_{38}FN_3O_6$ (519.6): MS (ESI$^+$) 520.52 (M+H$^+$).

Compound 28 (Example 16)

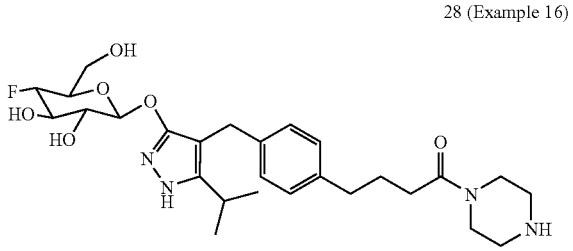

28 (Example 16)

Compound 28 is synthesized in analogy to the synthesis route described for compound 13 (example 2). Starting from the glycoside 10, which is, however, reacted not with n-butylamine but with benzyl 1-piperazine-carboxylate, compound 28 is obtained as a colorless wax. $C_{27}H_{39}FN_4O_6$ (534.6): MS (ESI$^+$) 535.32 (M+H$^+$).

Compound 29 (Example 17)

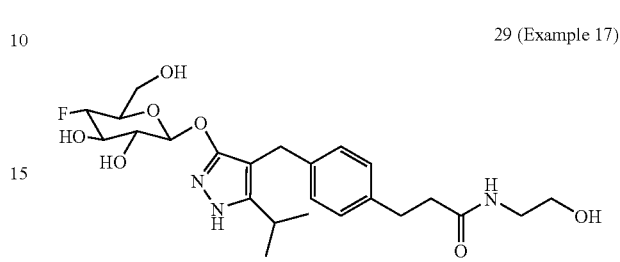

29 (Example 17)

Compound 29 is synthesized in analogy to the synthesis described for compound 19 (example 7). However, 3-aminopropionamide hydrochloride is replaced by 2-aminoethanol in the amide coupling. Compound 29 is obtained as a colorless oil. $C_{24}H_{34}FN_3O_7$ (495.6): MS (ESI$^+$) 496.43 (M+H$^+$).

Compound 30 (Example 18)

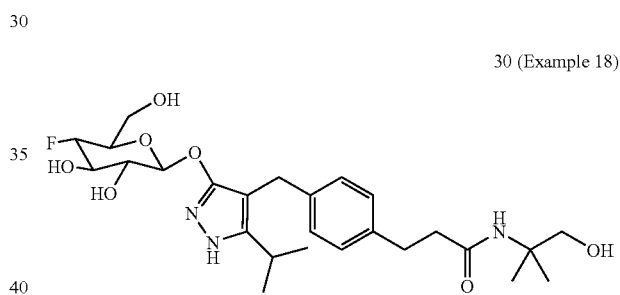

30 (Example 18)

Compound 30 is synthesized in analogy to the synthesis described for compound 19 (example 7). However, 3-aminopropionamide hydrochloride is replaced by 2-amino-2-methyl-1-propanol in the amide coupling. Compound 30 is obtained as a colorless oil. $C_{26}H_{38}FN_3O_7$ (523.6): MS (ESI$^+$) 524.26 (M+H$^+$).

Compound 31 (Example 19)

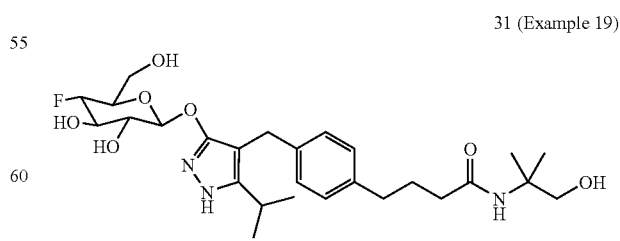

31 (Example 19)

Compound 31 is synthesized in analogy to the synthesis route described for compound 13 (example 2). Starting from the glycoside 10, which is, however, reacted not with n-butylamine but with 2-amino-2-methyl-1-propanol, compound 31 is obtained as a colorless solid. $C_{27}H_{40}FN_3O_7$ (537.6): MS (ESI$^+$) 538.28 (M+H$^+$).

Compound 32 (Example 20)

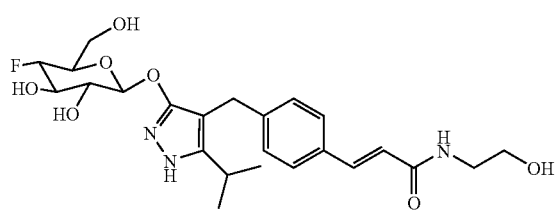

32 (Example 20)

Compound 32 is synthesized in analogy to the synthesis described for compound 29 (example 17). However, the hydrogenation stage is not carried out. Compound 32 is obtained as a colorless wax. $C_{24}H_{32}FN_3O_7$ (493.6): MS (ESI$^+$) 494.28 (M+H$^+$).

Compound 33 (Example 21)

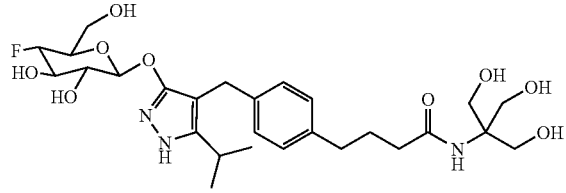

33 (Example 21)

Compound 33 is synthesized in analogy to the synthesis route described for compound 13 (example 2). Starting from the glycoside 10, which is, however, reacted not with n-butylamine but with tris(hydroxymethyl)-aminomethane, compound 33 is obtained as a colorless solid. $C_{27}H_{40}FN_3O_9$ (569.6): MS (ESI$^+$) 570.33 (M+H$^+$).

Compound 34 (Example 22)

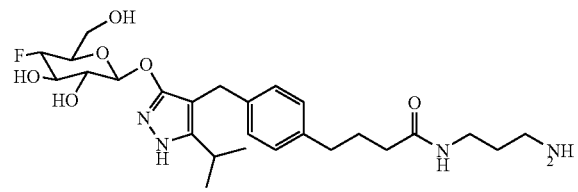

34 (Example 22)

Compound 34 is synthesized in analogy to the synthesis route described for compound 13 (example 2). Starting from the glycoside 10, which is, however, reacted not with n-butylamine but with N-carbobenzoxy-1,3-diaminopropane hydrochloride, compound 34 is obtained as a colorless oil.

$C_{26}H_{39}FN_4O_6$ (522.6): MS (ESI$^+$) 522.52 (M+H$^+$).

Compound 35 (Example 23)

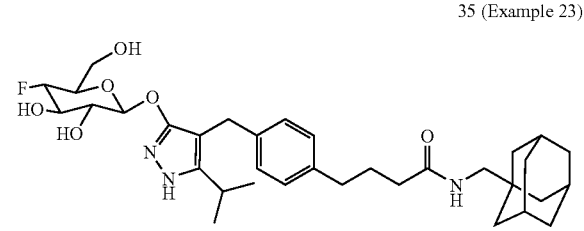

35 (Example 23)

Compound 35 is synthesized in analogy to the synthesis route described for compound 13 (example 2). Starting from the glycoside 10, which is, however, reacted not with n-butylamine but with 1-adamantane-methylamine, compound 35 is obtained as a colorless wax.

$C_{34}H_{48}FN_3O_6$ (613.8): MS (ESI$^+$) 614.45 (M+H$^+$).

Compound 36 (Example 24)

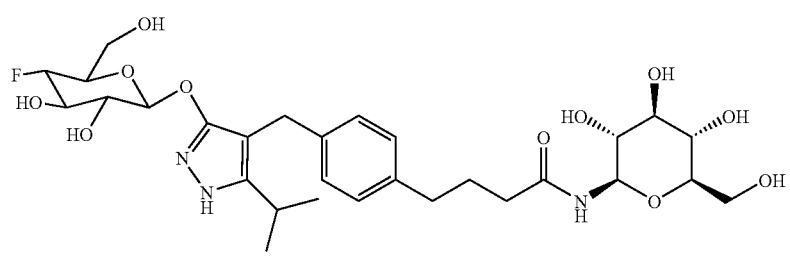

36 (Example 24)

Compound 36 is synthesized in analogy to the synthesis route described for compound 13 (example 2). Starting from the glycoside 10, which is, however, reacted not with n-butylamine but with 2,3,4,6-tetra-O-acetyl-1-amino-1-deoxy-beta-D-glucose, compound 36 is obtained as a colorless oil. $C_{29}H_{42}FN_3O_{11}$ (627.7): MS (ESI$^+$) 628.25 (M+H$^+$).

Compound 37 (Example 25)

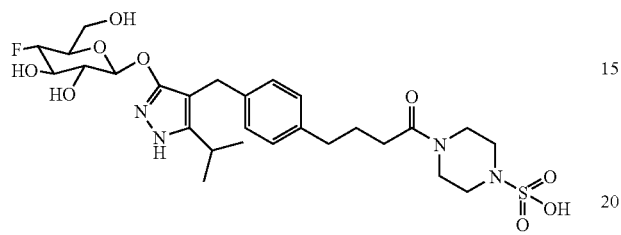

37 (Example 25)

Compound 37 is synthesized in analogy to the synthesis route described for compound 28 (example 16). However, the last stage, the deprotection with sodium methanolate, is preceded by reaction with sulfur trioxide-triethylamine complex: this is done by dissolving 63.0 mg of the piperazine compound in 10.0 ml of methanol and, at 0° C., adding 202 mg of sulfur trioxide triethylamine complex and stirring at 0° C. for 2 h. The solvent is removed in a rotary evaporator, and the crude product is purified on silica gel (methylene chloride/methanol/conc. ammonia=30/5/1). 59 mg of the sulfate compound are obtained and converted, in analogy to the synthesis of compound 28 with sodium methoxide, into the compound 37, which is obtained as a colorless wax. $C_{27}H_{39}FN_4O_9S$ (614.7): MS (ESI$^+$) 615.42 (M+H$^+$).

Compound 38 (Example 26)

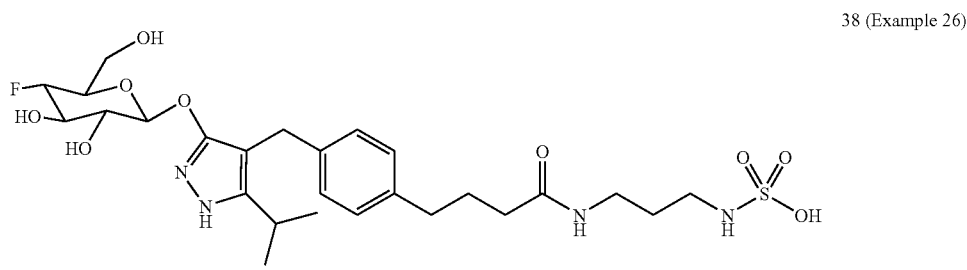

38 (Example 26)

Compound 38 is synthesized in analogy to the synthesis route described for compound 37 (example 25). Starting from the glycoside 10, which is, however, reacted not with benzyl 1-piperazinecarboxylate but with N-carbobenzoxy-1,3-diaminopropane hydrochloride, compound 38 is obtained as a colorless wax. $C_{26}H_{39}FN_4O_9S$ (602.7): MS (ESI$^+$) 603.41 (M+H$^+$).

Compound 39 (Example 27)

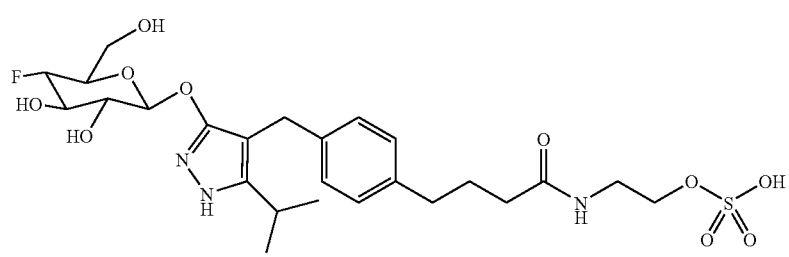

39 (Example 27)

Compound 39 is synthesized in analogy to the synthesis route described for compound 37 (example 25). Starting from the glycoside 10, which is, however, reacted not with benzyl 1-piperazinecarboxylate but with 2-aminoethanol, compound 39 is obtained as a colorless wax.

$C_{25}H_{36}FN_3O_{10}S$ (589.6): MS (ESI$^+$) 588.50 (M$^+$–H).

Compound 40 (Example 28)

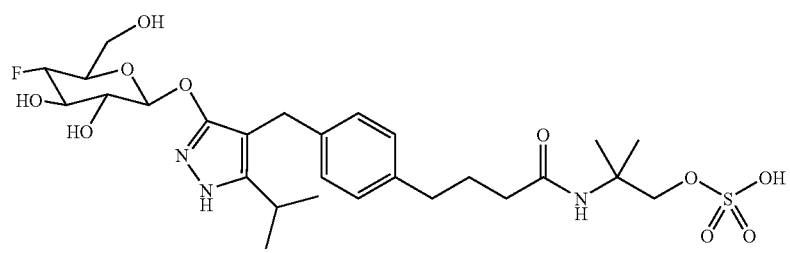

40 (Example 28)

Compound 40 is synthesized in analogy to the synthesis route described for compound 37 (example 25). Starting from the glycoside 10, which is, however, reacted not with benzyl 1-piperazinecarboxylate but with 2-amino-2-methyl-1-propanol, compound 40 is obtained as a colorless wax.

$C_{27}H_{40}FN_3O_{10}S$ (617.7): MS (ESI$^+$) 616.52 (M$^+$–H).

Compound 41 (Example 29)

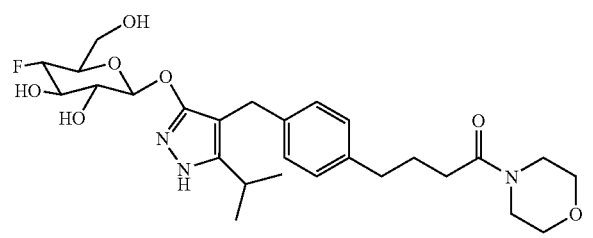

41 (Example 29)

Compound 41 is synthesized in analogy to the synthesis route described for compound 13 (example 2). Starting from the glycoside 10, which is, however, reacted not with n-butylamine but with morpholine, compound 41 is obtained as a pale yellow wax. $C_{27}H_{38}FN_3O_7$ (535.6): MS (ESI$^+$) 536.48 (M+H$^+$).

Compound 42 (Example 30)

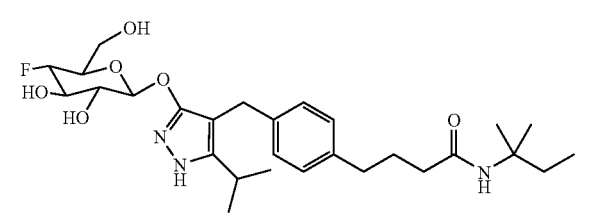

42 (Example 30)

Compound 42 is synthesized in analogy to the synthesis route described for compound 13 (example 2). Starting from the glycoside 10, which is, however, reacted not with n-butylamine but with tert-amylamine, compound 42 is obtained as a pale yellow wax. $C_{28}H_{42}FN_3O_6$ (535.7): MS (ESI$^+$) 536.54 (M+H$^+$).

Compound 43 (Example 31)

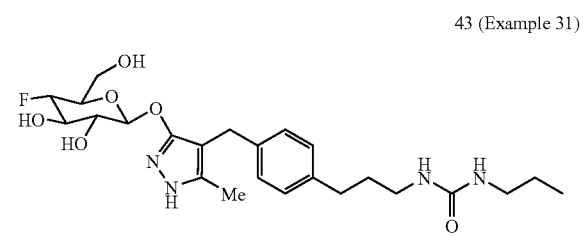

43 (Example 31)

41.3 mg of 1-allyl-3-propylurea are dissolved in 5.00 ml of THF, and 1.21 ml of a 0.5M 9-BBN solution in toluene are added, and the mixture is stirred at 20° C. for 4 h. Subsequently, a solution of 180 mg of the glycoside 17 in 10.0 ml of toluene, 7.4 mg of tri-o-tolylphosphine, 102.7 mg of potassium phosphate and 2.7 mg of Pd(OAc)$_2$ are added. The reaction mixture is heated at 100° C. for 3 h. The precipitate is filtered off, and the organic phase is washed with 10 ml of water and dried over magnesium sulfate. The solvent is removed in a rotary evaporator, and the crude product is purified by chromatography on silica gel (EtOAc/heptane). 59 mg of a colorless solid are obtained and reacted with sodium methoxide in analogy to the preparation of compound 13 (example 2). Compound 43 is obtained as a colorless wax. $C_{24}H_{35}FN_4O_6$ (494.6) MS (ESI$^+$) 494.12 (M$^+$).

4-(2-Ethoxycarbonyl-4-methyl-3-oxo-pent-1-enyl) benzoic acid (E/Z isomer mixture) (44)

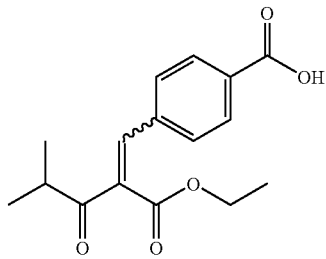

44

29.0 g of ethyl isobutyrylacetate and 33.0 g of 4-carboxybenzaldehyde are heated with a water trap for 6 h. The reaction solution is concentrated, taken up in ethyl acetate and extracted with 20% strength ammonium chloride solution and saturated sodium chloride solution. The organic phase is dried over magnesium sulfate, concentrated and directly reacted further to 45. 50.0 g of an oil are obtained. $C_{16}H_{18}O_5$ (290.3): MS (ESI$^+$): 291.1 (M+H)$^+$, $t_R$=1.42 min (Gradient 2).

4-(2-Ethoxycarbonyl-4-methyl-3-oxo-pentyl)benzoic acid (45)

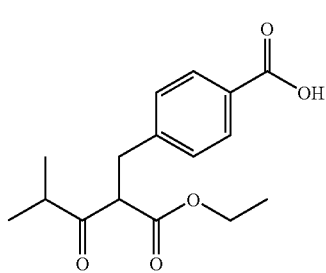

45

50 g of 4-(2-ethoxycarbonyl-4-methyl-3-oxo-pent-1-enyl) benzoic acid are dissolved in 300 ml of THF, 1.00 g of palladium on carbon (10%) is added, and the mixture is hydrogenated under a hydrogen pressure of 4 bar in an autoclave for 24 h. The mixture is diluted with dichloromethane and filtered with suction through Celite, the residue is washed with dichloromethane and concentrated in vacuo. The residue is purified by chromatography on silica gel (ethyl acetate/n-heptane=3/1). 45 g of compound 45 are obtained as an oil. $C_{16}H_{20}O_5$ (292.3) MS (ESI$^+$): 293.1 (M+H)$^+$, $t_R$=1.37 min (Gradient 2).

4-[1-(2-Cyanoethyl)-5-hydroxy-3-isopropyl-1H-pyrazol-4-ylmethyl]-benzoic acid (46)

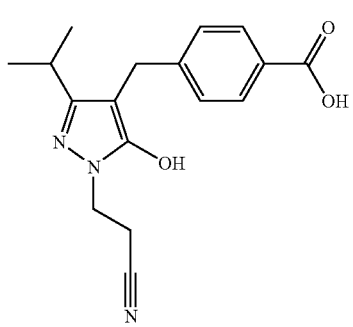

46

15 g of compound 45 are dissolved in 100 ml of glacial acetic acid. 7.4 ml of 2-cyanoethylhydrazine are added, and the solution is heated at 100° C. for 2 h. The mixture is added to ice-water and extracted several times with ethyl acetate. The organic phase is extracted with 20% strength ammonium chloride solution and saturated sodium chloride solution and dried over sodium sulfate. 2.40 g of the desired compound 46 crystallize out with the ethyl acetate phase. The mother liquor is concentrated and chromatographed on silica gel (dichloromethane:methanol:glacial acetic acid=100:10:1). A further 1.10 g of compound 46, plus 7.0 g of reisolated precursor 45, are obtained. $C_{17}H_{19}N_3O_3$ (313.4); MS (ESI$^+$): 314.2 (M+H)$^+$, $t_R$=0.97 min (Gradient 2).

N-(2-Carbamoylethyl)-4-[1-(2-cyano-ethyl)-5-hydroxy-3-isopropyl-1H-pyrazol-4-ylmethyl]benzamide (47)

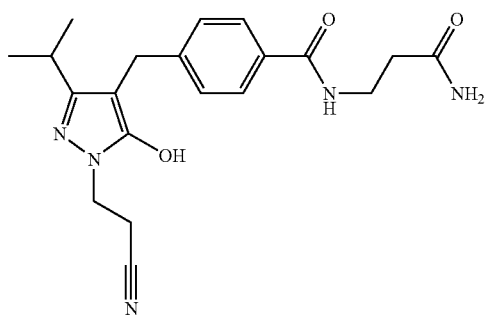

47

500 mg of compound 46 and 145 mg of □-alaninamide hydrochloride are introduced into 10 ml of dichloromethane, and 0.8 ml of N,N-diisopropylethylamine, 215 mg of 1-hydroxybenzotriazole and 306 mg of 1-ethyl-3-(3-dimethylaminopropyl)carbodiimide hydrochloride are added. The solution is stirred for 12 h. The solution is concentrated and the crude product is purified by chromatography on silica gel (dichloromethane/methanol/glacial acetic acid 100:0:5→100:10:5). 440 mg of the desired compound 47 are obtained. $C_{20}H_{25}N_5O_3$ (383.5); MS (ESI$^+$): 384.2 (M+H)$^+$, $t_R$=3.58 min (Gradient 3).

Compound 48

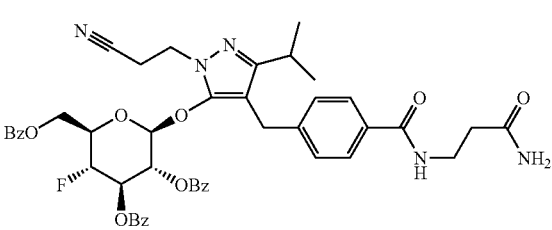

48

300 mg of compound 47, 436 mg of compound 4, and 324 mg of potassium carbonate are suspended in 25 ml of acetonitrile and 2.5 ml of water and stirred for 72 h. The reaction mixture is filtered, the residue is washed with dichloromethane, and the combined organic phase is extracted with water and saturated sodium chloride solution. The organic phase is dried over sodium sulfate and the residue is chromatographed on silica gel (dichloromethane/methanol=100/

5). 207 mg of the glycoside 48 are obtained as a colorless solid. $C_{47}H_{46}FN_5O_{10}$ (859.9); MS (ESI$^+$): 860.3 (M+H)$^+$, $t_R$=1.70 min (Gradient 2).

Compound 49 (Example 32)

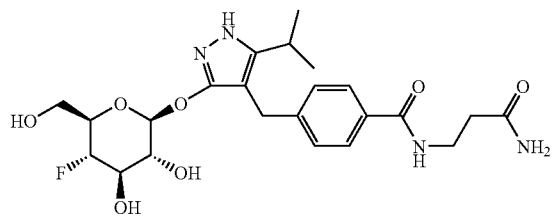

49 (Example 32)

200 mg of compound 48 are dissolved in 15 ml of THF and cooled to −78° C. under argon. 0.81 ml of lithium bis(trimethylsilyl)amide solution (1M in hexane) is slowly added through a septum. After 30 min, 2 ml of 20% strength ammonium chloride solution are added in the cold, and the solution is warmed to room temperature. 2 ml of saturated sodium chloride solution are added, the organic phase is separated off, and the aqueous phase is extracted twice with ethyl acetate. The combined organic phase is concentrated and the residue is taken up in a mixture of triethylamine: methanol: water (14 ml 1:3:3). The solution is stirred for 24 h and is then concentrated to dryness and purified by chromatography on silica gel. 50 mg of compound 49 are obtained as a colorless solid. $C_{23}H_{31}FN_4O_7$ (494.5); MS (ESI$^{31}$): 493.2 (M−H)$^-$, $t_R$=3.58 min (Gradient 3); $t_R$=0.97 min (Gradient 1).

Compound 50 (Example 33)

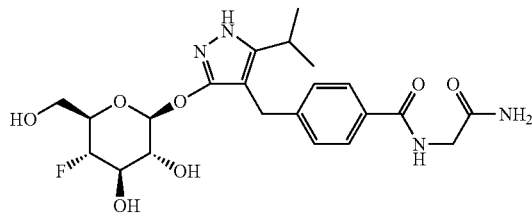

50 (Example 33)

Compound 50 is synthesized in analogy to the synthesis described for compound 49 (example 32). However, glycinamide hydrochloride is employed instead of P-alaninamide. Compound 50 is obtained as a colorless solid. $C_{22}H_{29}FN_4O_7$ (480.5): MS (ESI$^+$) 481.19 (M+H$^+$).

Compound 51 (Example 34)

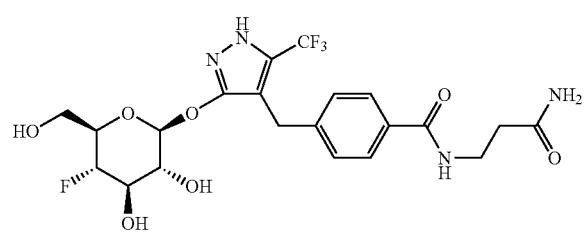

(Example 34)

51

Compound 51 is synthesized in analogy to the synthesis described for compound 49 (example 32). However, 4,4,4-trifluoroacetoacetate is used as starting material instead of ethyl isobutylacetate. Compound 51 is obtained as a colorless solid. $C_{21}H_{24}F_4N_4O_7$ (520.4): MS (ESI$^+$) 521.16 (M+H$^+$).

Compound 52 (Example 35)

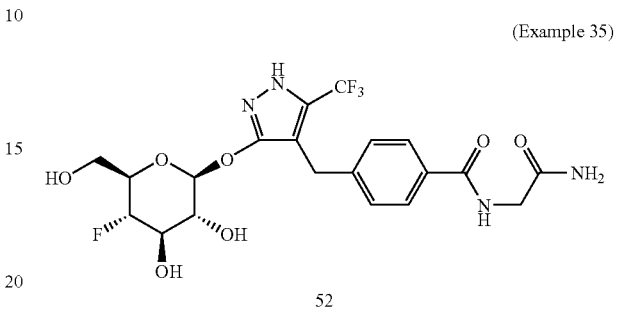

(Example 35)

52

Compound 52 is synthesized in analogy to the synthesis described for compound 50 (Example 33). However, 4,4,4-trifluoroacetoacetate is used as starting material instead of ethyl isobutylacetate. Compound 52 is obtained as a colorless solid. $C_{20}H_{22}F_4N_4O_7$ (506.4): MS (ESI$^+$) 507.16 (M+H$^+$).

Compound 53 (Example 36)

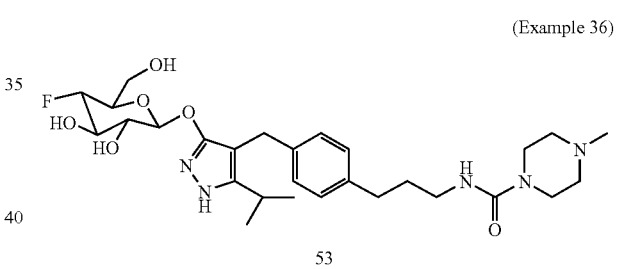

(Example 36)

53

Compound 53 is synthesized in analogy to the synthesis described for compound 43 (example 31), but 1-(N-methylpiperazine)-3-allylurea is used as starting material instead of 1-allyl-3-propylurea, and the glycoside 7 is employed instead of the glycoside 17. Compound 53 is obtained as a colorless solid. $C_{28}H_{42}FN_5O_6$ (563.7).

Compound 54 (Example 37)

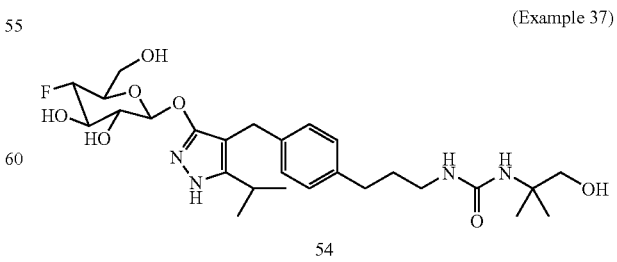

(Example 37)

54

Compound 54 is synthesized in analogy to the synthesis described for compound 43 (example 31), but 1-(N-methylpiperazine)-3-allylurea is used as starting material instead of 1-allyl-3-propylurea, and the glycoside 7 is employed instead of the glycoside 17. Compound 54 is obtained as a colorless solid. $C_{27}H_{41}FN_4O_7$ (552.7).

The invention claimed is:
1. A compound of formula I

I wherein:
R1 and R2 are, independently of one another, F or H, with the proviso that one of R1 or R2 must be F;

A is O, NH or S;

R3 is selected from hydrogen, F, Cl, Br, I, OH, $CF_3$, $NO_2$, CN, COOH, CO—$(C_1$-$C_6)$-alkyl, COO$(C_1$-$C_6)$-alkyl, $CONH_2$, CONH—$(C_1$-$C_6)$-alkyl, CON[$(C_1$-$C_6)$-alkyl]$_2$, $(C_1$-$C_6)$-alkyl, $(C_3$-$C_6)$-cycloalkyl, $(C_2$-$C_6)$-alkenyl, $(C_2$-$C_6)$-alkynyl, O—$(C_1$-$C_6)$-alkyl, HO—$(C_1$-$C_6)$-alkylene, $(C_1$-$C_6)$-alkylene-O—$(C_1$-$C_6)$-alkyl, phenyl, benzyl, $(C_1$-$C_6)$-alkoxycarbonyl, wherein any or all of the hydrogens of said alkyl, alkenyl, alkynyl and O-alkyl radicals may also be replaced by fluorine;

$SO_2$—$NH_2$, $SO_2$—NH$(C_1$-$C_6)$-alkyl, $SO_2$N[$(C_1$-$C_6)$-alkyl]$_2$, S—$(C_1$-$C_6)$-alkyl, S—$(CH_2)_o$-phenyl, SO—$(C_1$-$C_6)$-alkyl, SO—$(CH_2)_o$-phenyl, $SO_2$($C_1$-$C_6)$-alkyl, $SO_2$—$(CH_2)_o$-phenyl, wherein o is an integer from 0 to 6, and each said phenyl radical may be substituted up to twice by a substituent selected from F, Cl, Br, OH, $CF_3$, $NO_2$, CN, $OCF_3$, O—$(C_1$-$C_6)$-alkyl, $(C_1$-$C_6)$-alkyl, and $NH_2$;

$NH_2$, NH—$(C_1$-$C_6)$-alkyl, N($(C_1$-$C_6)$-alkyl)$_2$, NH—CO—$(C_1$-$C_7)$-alkyl, phenyl, O—$(CH_2)_o$-phenyl, wherein o is an integer from 0 to 6, and said phenyl ring may be substituted one to three times by a substituent selected from F, Cl, Br, I, OH, $CF_3$, $NO_2$, CN, $OCF_3$, O—$(C_1$-$C_6)$-alkyl, $(C_1$-$C_6)$-alkyl, $NH_2$, NH($C_1$-$C_6)$-alkyl, N(($C_1$-$C_6)$-alkyl)$_2$, $SO_2$—$CH_3$, COOH, COO—$(C_1$-$C_6)$-alkyl, and $CONH_2$;

R4 is selected from hydrogen, $(C_1$-$C_6)$-alkyl, $(C_2$-$C_6)$-alkenyl, $(C_3$-$C_6)$-cycloalkyl, and phenyl which phenyl may optionally be substituted by halogen or $(C_1$-$C_4)$-alkyl;

B is $(C_0$-$C_{15})$-alkylene, where one or more C atoms of the alkylene radical may be replaced independently of one another by —O—, —(C=O)—, —CH=CH—, —C≡C—, —S—, —CH(OH)—, —CHF—, —$CF_2$—, —(S=O)—, —($SO_2$)—, —N(($C_1$-$C_6)$-alkyl)-, —N(($C_1$-$C_6)$-alkylphenyl)- or —NH—;

R5, R6, R7 are independently of one another, selected from hydrogen, F, Cl, Br, I, OH, $CF_3$, $NO_2$, CN, COOH, COO($C_1$-$C_6)$-alkyl, CO($C_1$-$C_4)$-alkyl, $CONH_2$, CONH$(C_1$-$C_6)$-alkyl, CON[$(C_1$-$C_6)$-alkyl]$_2$, $(C_1$-$C_6)$-alkyl, $(C_2$-$C_6)$-alkenyl, $(C_2$-$C_6)$-alkynyl, O—$(C_1$-$C_8)$-alkyl, HO—$(C_1$-$C_6)$-alkylene, $(C_1$-$C_6)$-alkylene-O—$(C_1$-$C_6)$-alkyl, wherein any or all of the hydrogens of said alkyl, alkenyl, alkynyl and O-alkyl radicals may also be replaced by fluorine;

$SO_2$—$NH_2$, $SO_2$NH$(C_1$-$C_6)$-alkyl, $SO_2$N[$(C_1$-$C_6)$-alkyl]$_2$, S—$(C_1$-$C_6)$-alkyl, S—$(CH_2)_o$-phenyl, $SCF_3$, SO—$(C_1$-$C_6)$-alkyl, SO—$(CH_2)_o$-phenyl, $SO_2$($C_1$-$C_6)$-alkyl, $SO_2$—$(CH_2)_o$-phenyl, wherein o is an integer from 0 to 6, and said phenyl ring may be substituted one to two times by a substituent selected from F, Cl, Br, OH, $CF_3$, $NO_2$, CN, $OCF_3$, O—$(C_1$-$C_6)$-alkyl, $(C_1$-$C_6)$-alkyl, $NH_2$;

$NH_2$, NH—$(C_1$-$C_6)$-alkyl, N($(C_1$-$C_6)$-alkyl)$_2$, NH—CO—$(C_1$-$C_6)$-alkyl, phenyl, O—$(CH_2)_o$-phenyl, wherein o is an integer from 0 to 6, and said phenyl ring may be substituted one to three times by a substituent selected from F, Cl, Br, I, OH, $CF_3$, $NO_2$, CN, $OCF_3$, O—$(C_1$-$C_8)$-alkyl, $(C_1$-$C_6)$-alkyl, $NH_2$, NH($C_1$-$C_6)$-alkyl, N(($C_1$-$C_6)$-alkyl)$_2$, $SO_2$—$CH_3$, COOH, COO—$(C_1$-$C_6)$-alkyl, and $CONH_2$;

or

R6 and R7, together with the C atoms to which they are attached, form a 5 to 7 membered, saturated, partially or completely unsaturated ring, Cyc1, wherein 1 or 2 C atoms of the ring may also be replaced by N, O or S, and Cyc1 may optionally be substituted by a substituent selected from $(C_1$-$C_6)$-alkyl, $(C_2$-$C_5)$-alkenyl, $(C_2$-$C_5)$-alkynyl;

wherein, in each case, one $CH_2$ group may be replaced by O, or substituted by a substituent selected from H, F, Cl, OH, $CF_3$, $NO_2$, CN, COO($C_1$-$C_4)$-alkyl, $CONH_2$, CONH($C_1$-$C_4)$-alkyl, and $OCF_3$;

X is CO, O, NH, S, SO, $SO_2$ or a bond;

L is selected from $(C_1$-$C_6)$-alkylene, $(C_2$-$C_5)$-alkenylene, and $(C_2$-$C_5)$-alkynylene, wherein, in each case, one or two $CH_2$ group(s) may be replaced by O or NH;

Y is CO, NHCO, SO, $SO_2$, or a bond;

R8, and R9, independently of one another, are selected from hydrogen, $SO_3H$, sugar residue, $(C_1$-$C_6)$-alkyl, wherein one or more $CH_2$ groups of the alkyl radical may be substituted, independently of one another, by a substituent selected from $(C_1$-$C_6)$-alkyl, OH, $(C_1$-$C_6)$-alkylene-OH, $(C_2$-$C_6)$-alkenylene-OH, O-sugar residue, $OSO_3H$, $NH_2$, NH—$(C_1$-$C_6)$-alkyl, N[$(C_1$-$C_6)$-alkyl]$_2$, NH—CO—$(C_1$-$C_6)$-alkyl, NH-sugar residue, NH—$SO_3H$, $(C_1$-$C_6)$-alkylene-$NH_2$, $(C_2$-$C_6)$-alkenylene-$NH_2$, $(C_0$-$C_6)$-alkylene-COOH, $(C_0$-$C_6)$-alkylene-$CONH_2$, $(C_0$-$C_6)$-alkylene-CONH—$(C_1$-$C_6)$-alkyl, $(C_0$-$C_6)$-alkylene-$SONH_2$, $(C_0$-$C_6)$-alkylene-SONH—$(C_1$-$C_6)$-alkyl, $(C_0$-$C_6)$-alkylene-$SO_2NH_2$, $(C_0$-$C_6)$-alkylene-$SO_2$NH—$(C_1$-$C_6)$-alkyl, and adamantyl; or R8 and R9, together with the N atom to which they are attached, form a 5 to 7 membered, saturated ring, Cyc2, wherein one or more $CH_2$ groups of the ring may also be replaced by O, S, NH, $NSO_3H$, N-sugar residue, or N—$(C_1$-$C_6)$-alkyl, wherein one or more $CH_2$ groups of the alkyl radical may be substituted, independently of one another, by a substituent selected from $(C_1$-$C_6)$-alkyl, OH, $(C_1$-$C_6)$-alkylene-OH, $(C_2C_6)$-alkenylene-OH, $NH_2$, NH—$(C_1$-$C_6)$-alkyl, N[$(C_1$-$C_6)$-alkyl]$_2$, NH—CO—$(C_1$-$C_6)$-alkyl, NH-sugar residue, $(C_1-C_6)$-alkylene-$NH_2$, $(C_2-C_6)$-alkenylene-$NH_2$, $(C_0-C_6)$-alkylene-COOH, $(C_0-C_6)$-alkylene-$CONH_2$, $(C_0-C_6)$-alkylene-CONH—$(C_1-C_6)$-alkyl, $(C_0-C_6)$-alkylene-$SONH_2$, $(C_0-C_6)$-alkylene-SONH—$(C_1-C_6)$-alkyl, $(C_0-C_6)$-alkylene-$SO_2NH_2$, and $(C_0-C_6)$-alkylene-$SO_2$NH—$(C_1-C_6)$-alkyl;

and the pharmaceutically acceptable salts thereof.

2. A compound of formula I as claimed in claim 1, in which:

A is O or NH;

R3 is selected from hydrogen, F, Cl, Br, I, OH, $CF_3$, $NO_2$, CN, COOH, CO—$(C_1-C_6)$-alkyl, COO$(C_1-C_6)$-alkyl, $CONH_2$, CONH—$(C_1-C_6)$-alkyl, CON$[(C_1-C_6)$-alkyl$]_2$, $(C_1-C_6)$-alkyl, $(C_2-C_6)$-alkenyl, $(C_2-C_6)$-alkynyl, O—$(C_1-C_6)$-alkyl, HO—$(C_1-C_6)$-alkylene, $(C_1-C_6)$-alkylene-O—$(C_1-C_6)$-alkyl, phenyl, benzyl, $(C_1-C_4)$-alkylene-COOH, and SO—$(C_1-C_6)$-alkyl, wherein any or all of the hydrogens of said alkyl radicals may be replaced by fluorine;

R4 is selected from hydrogen, $(C_1-C_6)$-alkyl, $(C_2-C_6)$-alkenyl, and $(C_3-C_6)$-cycloalkyl;

B is $(C_0-C_6)$-alkylene, wherein one or more C atoms of the alkylene radical may be replaced, independently of one another, by —O—, —(C=O)—, —CH=CH—, —C≡C—, —S—, —CH(OH)—, —CHF—, —$CF_2$—, —(S=O)—, —($SO_2$)—, —N(($C_1-C_6$)-alkylene-, —N(($C_1-C_6$)-alkylene-phenylene)- or —NH—.

3. A compound of formula I as claimed in claim 1, in which the sugar residues are beta(β)-linked, and the stereochemistry in the 2, 3 and 5 positions of the sugar residue has the D-gluco configuration.

4. A compound of formula I as claimed in claim 1, in which:

R1 is hydrogen and R2 is fluorine; or
R1 is fluorine and R2 is hydrogen;
A is O, or NH;

R3 is selected from hydrogen, F, Cl, Br, I, OH, $CF_3$, $(C_1-C_6)$-alkyl, $(C_3-C_6)$-cycloalkyl, $(C_2-C_6)$-alkenyl, and O—$(C_1-C_6)$-alkyl, wherein any or all of the hydrogens of said alkyl radicals may be replaced by fluorine;

R4 is hydrogen, $(C_1-C_6)$-alkyl, or $(C_3-C_6)$-cycloalkyl;

B is $(C_1-C_4)$-alkylene, wherein one or more C atoms of the alkylene radical may be replaced, independently of one another, by —O—, —(C=O)—, —CH=CH—, —CH(OH)—, —CHF—, —$CF_2$— or —NH—;

R5, R6, R7, independently of one another, are selected from hydrogen, F, Cl, Br, I, OH, $CF_3$, $NO_2$, CN, COOH, COO$(C_1-C_6)$-alkyl, CO$(C_1-C_4)$-alkyl, $CONH_2$, CONH$(C_1-C_6)$-alkyl, CON$[(C_1-C_6)$-alkyl$]_2$, $(C_1-C_6)$-alkyl, $(C_2-C_6)$-alkenyl, $(C_2-C_6)$-alkynyl, O—$(C_1-C_8)$-alkyl, HO—$(C_1-C_6)$-alkylene, and $(C_1-C_6)$-alkylene-O—$(C_1-C_6)$-alkyl, wherein any or all of the hydrogens of said alkyl, alkenyl, alkynyl and O-alkyl radicals may be replaced by fluorine;

$NH_2$, NH—$(C_1-C_6)$-alkyl, N(($C_1-C_6$)-alkyl)$_2$, NH—CO—$(C_1-C_6)$-alkyl, or R6 and R7, together with the C atoms to which they are attached, form a 5 to 7 membered, saturated, partially or completely unsaturated ring, Cy1, wherein 1 or 2 C atom(s) of the ring may also be replaced by N, O or S, and Cyc1 may optionally be substituted by $(C_1-C_6)$-alkyl, $(C_2-C_5)$-alkenyl, or $(C_2-C_5)$-alkynyl, wherein, in each case, one $CH_2$ group may be replaced by O, or substituted by H, F, Cl, OH, $CF_3$, $NO_2$, CN, COO$(C_1-C_4)$-alkyl, $CONH_2$, CONH$(C_1-C_4)$-alkyl, or $OCF_3$;

X is CO, O, NH, or a bond;

L is $(C_1-C_6)$-alkylene, or $(C_2-C_5)$-alkenylene, wherein one or two $CH_2$ groups may be replaced by O or NH; and Y is CO, NHCO, a bond.

5. A compound of formula I as claimed in claim 1, in which:

R1 is hydrogen;
R2 is fluorine;
A is O;
R3 is $CF_3$, methyl, or isopropyl;
R4 is hydrogen;
B is $(C_1-C_4)$-alkylene, wherein one or more C atoms of the alkylene radical may be replaced, independently of one another, by —O—, —(C=O)—, —CHF— or —$CF_2$—;

X is CO, O, or a bond;

L is $(C_1-C_4)$-alkylene, or $(C_2-C_4)$-alkenylene, wherein, in each case, one or two $CH_2$ groups may be replaced by O or NH; and Y is CO, NHCO, or a bond.

6. A compound of formula I as claimed in claim 1, in which:

R1 is hydrogen;
R2 is fluorine;
A is O;
B is —$CH_2$—;
R5 is hydrogen, Cl, methyl, ethyl, OH, or $CF_3$;
R6 and R7 are each hydrogen;
X is CO, O, or a bond;

L is $(C_1-C_3)$-alkylene, or $(C_2-C_3)$-alkenylene, wherein, in each case, one $CH_2$ group may be replaced by O or NH;

Y is CO, NHCO, or a bond.

7. A compound of formula I as claimed in claim 1, in which the substituents A and B are ortho to each other and R3 is ortho to B.

8. A compound of formula I as claimed in claim 1, in which:

R8 and R9 are, independently of one another, selected from hydrogen, $SO_3H$, sugar residue, and $(C_1-C_4)$-alkyl, wherein the alkyl radicals may be substituted, independently of one another, one or more times, by $(C_1-C_2)$-alkyl, OH, $(C_1-C_2)$-alkylene-OH, $OSO_3H$, $NH_2$, $CONH_2$, $SO_2NH_2$, NH—$SO_3H$ or adamantyl; or R8 and R9, together with the N atom to which they are attached, form a 5 to 7 membered, saturated ring, Cyc2, said Cyc2 being selected from the group consisting of piperazine, which piperazine may be N-substituted by $(C_1-C_2)$-alkyl, $(C_1-C_2)$-alkylene-OH or $SO_3H$, piperidine, azepane, pyrrolidine and morpholine.

9. A medicament comprising at least one compound as claimed in claim 1.

10. The medicament of claim 9, further comprising one or more blood glucose-lowering active ingredients.

11. A medicament as claimed in claim 9, which further comprises a pharmaceutically suitable carrier.

12. A method for the treatment of type 1 and type 2 diabetes comprising administering to a patient in need thereof an effective amount of a medicament as claimed in claim 9.

13. A method for lowering blood glucose comprising administering to a patient in need thereof an effective amount of a medicament as claimed in claim 9.

14. A method for the treatment of type 1 and type 2 diabetes comprising administering to a patient in need thereof an effective amount of a medicament as claimed in claim 10.

15. A method for lowering blood glucose comprising administering to a patient in need thereof an effective amount of a medicament as claimed in claim 10.

* * * * *

UNITED STATES PATENT AND TRADEMARK OFFICE
CERTIFICATE OF CORRECTION

PATENT NO. : 7,820,804 B2
APPLICATION NO. : 11/567410
DATED : October 26, 2010
INVENTOR(S) : Harm Brummerhop et al.

It is certified that error appears in the above-identified patent and that said Letters Patent is hereby corrected as shown below:

On the cover page, item (73), in column 1, line 1, delete "Aventia" and insert -- Aventis --, therefor.

In column 3, line 17, delete "$SO_2N$ H" and insert -- $SO_2NH$ --, therefor.

In column 3, line 25, delete "$(C_2C_6)$" and insert -- $(C_2-C_6)$ --, therefor.

In column 7, line 56, delete "bufter," and insert -- buffer, --, therefor.

In column 8, line 61, delete "mefformin." and insert -- metformin. --, therefor.

In column 9, line 12, delete "TSO21" and insert -- TS021 --, therefor.

In column 9, line 30, delete "mefformin," and insert -- metformin, --, therefor.

In column 13, line 42, delete "Accesion" and insert -- Accession --, therefor.

In column 14, line 2, delete "1 pg/ml" and insert -- -1 µg/ml --, therefor.

In column 14, line 22-23, delete "82 l/well" and insert -- µl/well --, therefor.

In column 14, line 27, delete "(IC50)" and insert -- ($IC_{50}$) --, therefor.

In column 14, line 46, delete "(IC50)." and insert -- ($IC_{50}$). --, therefor.

In column 14, line 47, delete "IC50" and insert -- $IC_{50}$ --, therefor.

In column 15-16, in Table 1, line 14, delete "538.56" and insert -- 548.56 --, therefor.

In column 17, line 3, delete "aceronitrile" and insert -- acetonitrile --, therefor.

In column 17, line 3, after "0.05%" insert -- TFA:water+0.05% --.

In column 17, line 3, delete "( min)" and insert -- (0 min) --, therefor.

Signed and Sealed this
Twenty-fourth Day of May, 2011

David J. Kappos
*Director of the United States Patent and Trademark Office*

CERTIFICATE OF CORRECTION (continued)

In column 17, line 4, delete "(2.3 min)" and insert -- (2.5 min) --, therefor.

In column 17, line 4, delete "33×4" and insert -- 33×2, 4 --, therefor.

In column 17, line 5, after "(gradient 1)" insert -- . --.

In column 17, line 17, delete "mm)," and insert -- mm). --, therefor.

In column 18, line 37, delete "gl ucopyranoside" and insert -- glucopyranoside --, therefor.

In column 28, line 22, delete "(scheme 1)." and insert -- (scheme I). --, therefor.

In column 34, line 10, delete " 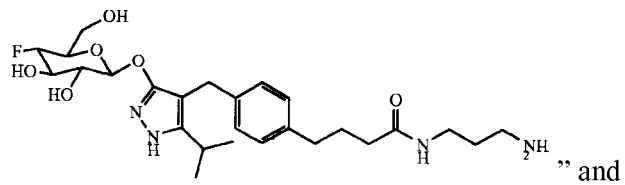 " and insert -- 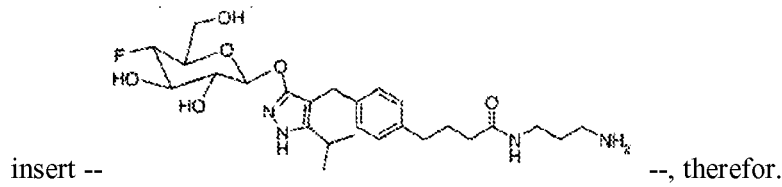 --, therefor.

In column 41, line 50, delete "P-alaninamide." and insert -- β-alaninamide. --, therefor.

In column 44, line 55, in claim 1, delete "S0$_2$NH$_2$," and insert -- SO$_2$NH$_2$, --, therefor.

In column 44, line 66, in claim 1, delete "(C$_2$C$_6$)" and insert -- (C$_2$-C$_6$) --, therefor.

In column 45, line 63, in claim 4, delete "Cy1," and insert -- Cyc1, --, therefor.